United States Patent
Goetsch et al.

(10) Patent No.: US 9,676,839 B2
(45) Date of Patent: Jun. 13, 2017

(54) PROCESS FOR THE MODULATION OF THE ANTAGONISTIC ACTIVITY OF A MONOCLONAL ANTIBODY

(75) Inventors: Liliane Goetsch, Ayze (FR); Thierry Wurch, Machilly (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 1257 days.

(21) Appl. No.: 13/131,907

(22) PCT Filed: Dec. 2, 2009

(86) PCT No.: PCT/EP2009/066205
§ 371 (c)(1),
(2), (4) Date: May 31, 2011

(87) PCT Pub. No.: WO2010/063746
PCT Pub. Date: Jun. 10, 2010

(65) Prior Publication Data
US 2011/0263830 A1    Oct. 27, 2011

(30) Foreign Application Priority Data
Dec. 2, 2008  (WO) ............... PCT/IB2008/055664

(51) Int. Cl.
C07K 16/00 (2006.01)
C07K 16/28 (2006.01)
C07K 1/107 (2006.01)
A61K 39/00 (2006.01)

(52) U.S. Cl.
CPC ............... *C07K 16/00* (2013.01); *C07K 1/107* (2013.01); *C07K 16/2863* (2013.01); *A61K 2039/505* (2013.01); *C07K 2317/24* (2013.01); *C07K 2317/53* (2013.01); *C07K 2317/73* (2013.01); *C07K 2317/75* (2013.01); *C07K 2317/76* (2013.01)

(58) Field of Classification Search
None
See application file for complete search history.

(56) References Cited

U.S. PATENT DOCUMENTS

2007/0014802 A1* 1/2007 Heywood et al. ......... 424/155.1

FOREIGN PATENT DOCUMENTS

| EP | 1707627 A1 | 10/2006 |
|---|---|---|
| WO | WO2005063981 A1 | 7/2005 |
| WO | WO2006116260 A2 | 11/2006 |
| WO | WO2007011941 A2 | 1/2007 |
| WO | WO2007011941 A3 | 1/2007 |
| WO | WO2007016285 A2 | 2/2007 |
| WO | WO2007126799 A2 | 11/2007 |
| WO | WO2007126799 A3 | 11/2007 |

OTHER PUBLICATIONS

Cavacini, L. A. et al., "Influence of Heavy Chain Constant Regions on Antigen Binding and HIV-1 Neturalization by a Human Monoclonal Antibody," *J. Immuno.*, 155:3638-3644 (1995).
Dall' Acqua, W. F. et al., "Modulation of the Effector Functions of a Human IgG1 Through Engineering of Its Hinge Region," *J. of Immuno.*, 177:1129-1138 (2006).
International Seach Report for International Application No. PCTEP2009066205, dated Apr. 20, 2010.

* cited by examiner

*Primary Examiner* — Brad Duffy
(74) *Attorney, Agent, or Firm* — Finnegan, Henderson, Farabow, Garrett & Dunner L.L.P.

(57) ABSTRACT

The present disclosure relates to the antibody engineering field and, more particularly, to a process for the screening of antibodies and/or the modulation of the agonistic/antagonistic activity of antibodies. More particularly, the disclosure concerns a process of improving the antagonistic activity of a monoclonal antibody directed against a specific target molecule, or a divalent functional fragment or derivative thereof, the antibody being capable of inhibiting one or more of the biological activities of the target molecule, wherein the process comprises a stage of reconfiguration of the hinge region consisting of a modification of the amino acid sequence of the hinge region by the deletion, the addition or the substitution of at least one amino acid. The disclosure also relates to polypeptides useful for such a modulation method and the obtained antibodies.

7 Claims, 15 Drawing Sheets

PROCESS FOR THE MODULATION OF THE ANTAGONISTIC ACTIVITY OF A MONOCLONAL ANTIBODY

Figure 1A:
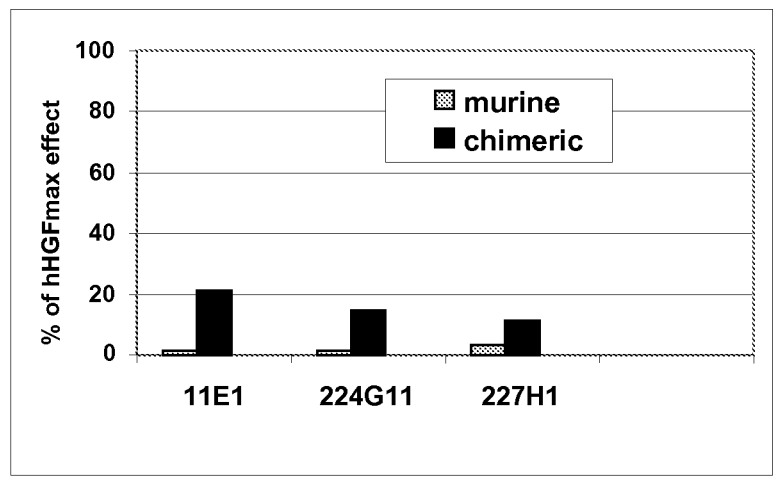

The present invention relates to the antibody engineering field and, more particularly, to a process for the screening of antibodies and/or the modulation of the agonistic/antagonistic activity of antibodies. More particularly, the invention concerns a method for the modulation of the antagonistic activity of a monoclonal antibody, or a divalent functional fragment or derivative thereof by genetic engineering. The invention also relates to polypeptides useful for such a modulation method and the obtained antibodies.

The terms "antibody", "antibodies" or "immunoglobulin" are used interchangeably in the broadest sense and include monoclonal antibodies (e.g., full length or intact monoclonal antibodies), polyclonal antibodies, multivalent antibodies or multispecific antibodies (e.g., bispecific antibodies so long as they exhibit the desired biological activity).

More particularly, such molecule consists in a glycoprotein comprising at least two heavy (H) chains and two light (L) chains inter-connected by disulfide bonds. Each heavy chain is comprised of a heavy chain variable region (or domain) (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immunue system (e.g. effector cells) and the first component (Clq) of the classical complement system.

The heavy chains of immunoglobulins can be divided into three functional regions: the Fd region, the hinge region, the Fc region (fragment crystallizable) which are connected by a flexible hinge region. The Fd region comprises the VH and CH1 domains and, in combination with the light chain, forms Fab—the antigen-binding fragment. The Fc fragment is responsible for the immunoglobulin effector functions, which include, for example, complement fixation and binding to cognate Fc receptors of effector cells. The hinge region, found in IgG, IgA, and IgD immunoglobulin classes, acts as a flexible spacer that allows the Fab portion to move freely in space relative to the Fc region. In contrast to the constant regions, the hinge domain is structurally diverse, varying in both sequence and length among immunoglobulin classes and subclasses.

According to crystallographic studies, the immunoglobulin hinge region can be further subdivided structurally and functionally into three regions: the upper hinge, the core, and the lower hinge (Shin et al., Immunological Reviews 130:87, 1992). The upper hinge includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges. The lower hinge region joins the amino terminal end of, and includes residues in, the CH2 domain. The core hinge region of human IgG1 contains the sequence Cys-Pro-Pro-Cys that, when dimerized by disulfide bond formation, results in a cyclic octapeptide believed to act as a pivot, thus conferring flexibility. Conformational changes permitted by the structure and flexibility of the immunoglobulin hinge region polypeptide sequence may affect the effector functions of the Fc portion of the antibody.

In general, for the preparation of monoclonal antibodies or their functional fragments, of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975). Then, the monoclonal antibodies can, for example, be purified on an affinity column on which the receptor of interest or one of its fragments containing the epitope specifically recognized by said monoclonal antibodies has previously been immobilized. More particularly, said monoclonal antibodies can be purified by chromatography on protein A and/or G, followed or not followed by ion-exchange chromatography aimed at eliminating the residual protein contaminants as well as the DNA and the LPS, in itself followed or not followed by exclusion chromatography on Sepharose gel in order to eliminate the potential aggregates due to the presence of dimers or of other multimers. In an even more preferred manner, the whole of these techniques can be used simultaneously or successively.

By functional fragment of an antibody according to the invention, it is intended to indicate in particular an antibody fragment, such as Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the original antibody.

Preferably, these functional fragments will be fragments of Fv, scFv, Fab, F(ab')$_2$, F(ab'), scFv-Fc type or diabodies, which generally have the same specificity of binding as the antibody from which they are descended. According to the present invention, antibody fragments of the invention can be obtained starting from antibodies such as described above by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applera, etc.

The term "antagonist" as used herein refers to a molecule which is capable of inhibiting one or more of the biological activities of a target molecule, such as an extracellular or transmembranar receptor. Antagonists may act by interfering with the binding of a receptor to a ligand and vice versa, by decreasing receptor phosphorylation, and/or by incapacitating or killing cells which have been activated by a ligand. The antagonist may completely block receptor-ligand interactions or may substantially reduce such interactions by competition, change of conformation, shedding or downregulation. All such points of intervention by an antagonist shall be considered equivalent for purposes of this invention.

The term "agonist" as used herein refers to any compound, including a protein, a polypeptide, a peptide, an antibody, an antibody fragment, a conjugate, a large molecule, a small molecule, capable of activating one or more of the biological activities of a target molecule.

In the research of therapeutic antibodies, it is often expected to have antibodies as antagonist as possible.

Classical examples of antagonist antibodies are Herceptin, Pertuzumab, Cetuximab, anti-VEGFR or anti-IGF-1R antibodies.

As a particular example, it can be mentioned the anti-c-Met 5D5 antibody generated by Genentech [WO 96/38557] which behaves as a potent agonist when added alone in various models. In order to solve this technical problem, this antibody had to be engineered as a Fab fragment or as a monovalent antibody (one-armed 5D5) to have an antagonistic activity. As a consequence, such antibody can not be considered as an antibody, but a fragment, and does not present all advantages due to the "full antibody" format (no effector functions, reduced clearance and half-life [2 times faster than traditional bivalent antibodies as described in Poster 411 at the 20th EORTC-NCI-AACR symposium, Geneva, Oct. 21-24, 2008]).

The skilled artisan will recognize that effector functions include, for example, C1q binding; complement dependent cytotoxicity; Fc receptor binding; antibody-dependent cell-mediated cytotoxicity (ADCC); phagocytosis; and down regulation of cell surface receptors (e.g. B cell receptor; BCR) and prolonging half-life through incorporation of the salvage receptor binding ligand (FcRn) as described in, for example, U.S. Pat. No. 5,739,277 issued Apr. 14, 1998.

One of the inventive aspects of the present invention is to solve such technical problems, i.e. improving the antagonistic activity of an antibody while preserving a "full divalent" format.

It must be mentioned herein that the invention can be applied to modulate the agonistic/antagonistic activity of human antibodies obtained by immunization of "human mice" (genetically modified mice that produce human immunoglobulins) or using phage display techniques to build whole antibodies from selected scFv, Fab or any other equivalent fragments.

Another classical technical problem can be met in the course of chimerization and/or humanization of a murine antibody. It is well known by the man skilled in the art that, if the chimerization and/or humanization process of a murine antibody, is quite easy in the theory, it is not so easy to manage the chimerization and/or humanization of such a murine antibody without losing all or part of initial properties. Chimeric or humanized antibody may lose part of its ADCC, CDC, antagonistic/agonistic, binding, (TBC) . . . activities. The present invention concerns, more particularly, the modification of agonistic/antagonistic activity of a murine antibody after a chimerization and/or humanization process.

As a particular example, a set of anti-cMet antibodies, thereafter described as 224G11, 2274H1 and 11E1, that behave as potent antagonist murine antibodies became partial agonists when chimerized on a human IgG1 format. This shift from potent antagonists to partial agonists resulted in a complete loss of in vivo activity in xenograft models.

The present invention intends to solve these problems and relates more particularly to a process of improving the antagonistic activity of a monoclonal antibody directed against a specific target molecule, or a divalent functional fragment or derivative thereof, said antibody being capable of inhibiting one or more of the biological activities of said target molecule, wherein said process comprises a stage of reconfiguration of the hinge region consisting of a modification of the amino acid sequence of said hinge region by the deletion, the addition or the substitution of at least one amino acid.

It is clear that the expression "improving the antagonistic activity" must be interpreted in its broadest sense, i.e. as the wanted result. Mechanistically, such result can be obtained by an improvement of the intrinsic antagonistic activity and/or a decrease of the intrinsic agonistic activity of an antibody.

More particularly, basic definitions of terms in quantitative pharmacology are based on the updated recommendations given by the International Union of Pharmacology (IUPHAR) Committee on receptor Nomenclature (see Neubig et al., 2003).

The term 'agonist' stands for a ligand (any type of molecule) that binds to a receptor and alters the receptor state resulting in a stimulatory or increased biological response. Agonists can act as full agonists or partial agonists:

Full agonist: when the receptor stimulus induced by an agonist reaches the maximal response capability of the system, then it will produce the system maximal response and be a full agonist in that system. Several agonists may elicit the same maximal response, they are all full agonists in that experimental system.

Partial agonist: a molecule that in a given tissue, under specified conditions, cannot elicit as large an effect (even when applied at high concentration, so that all the receptors should be occupied) as can a full agonist acting through the same receptors in the same system. Partial agonists are generally also partial antagonists since in the co-presence of a full agonist, they reduce the maximal response of the said full agonist to their own maximal response. This designation of full vs. partial agonist is system-dependent, and a full agonist for one system or measurement may be a partial agonist in another.

The term 'antagonist' stands for a molecule that reduces the action of another drug, generally an agonist. Many antagonists act at the same receptor macromolecule as the agonist.

The efficacy of antagonism can be full antagonism where the response of the system in the co-presence of the antagonist and agonist corresponds to the basal (without any ligand) activity of the system.

An antagonist can act as partial antagonist when the maximal inhibition (even when applied at high concentration, so that all the receptors should be occupied by the antagonist) elicited by the co-presence of the antagonist and agonist is above the basal activity of the system.

Antagonism can be competitive when the binding of agonist and antagonist is mutually exclusive. This may be because the agonist and antagonist compete for the same binding site or combine with adjacent sites that overlap. A third possibility is that different sites are involved but that they influence the receptor macromolecule in such a way that agonist and antagonist molecules cannot be bound at the same time.

Noncompetitive antagonism is observed when agonist and antagonist can be bound to the receptor simultaneously; antagonist binding reduces or prevents the action of the agonist with or without any effect on the binding of the agonist.

The deletion, addition or substitution can be classically done by any method known by the skilled artisan.

Several methods can be applied by the skilled artisan to generate additions, deletions or insertions in a given DNA sequence. Can be mentioned without limitations, partial digestion of DNA with pancreatic DNAse I, partial digestion of DNA with restriction enzymes, linker-based insertions mutants, nested sets of deletion mutants using BAL31 nuclease, DNAse I or exonuclease III. These methods are extensively described in laboratory manuals such as Molecular Cloning, A laboratory manual (Sambrook, Fritsch and Maniatis). Several PCR-based methods can also be employed to generate deletions, insertions or site-directed mutagenesis in a DNA molecule such as overlap extension PCR (Wurch et al., 1998), but not limited to this one. To perform site directed mutagenesis, several other techniques can be used, as examples, but not limited to these ones, can be mentioned oligonucleotide based mutagenesis based on either single or double-primer methods, the Kunkel method based on uracil incorporation (Kunkel, 1985). These methods are extensively described in laboratory manuals such as Molecular Cloning, A laboratory manual (Sambrook, Fritsch and Maniatis).

As a non limitative example of addition, it can be mentioned the addition of a Proline into or adjacent to the hinge region.

In a preferred embodiment of the process of the invention, said modification is selected from:
  i) the deletion of at least one amino acid of said hinge region amino acid sequence; and/or
  ii) the addition of at least one disulfide bridge into said hinge region.

In order to clarify the invention, the first aspect (i) will be detailed in first and the second aspect (ii) will be detailed after. It must be understood that this ordering is only due to the writing of the present application and that both of these aspects, as it will be obvious hereinafter, are of similar importance.

In a particular embodiment, a way to modify the amino acid sequence of the hinge region will consists of the deletion of at most 2, 3 or 4 amino acids of said hinge region amino acid sequence.

A particular aspect of the invention is that said monoclonal antibody is a divalent antibody. Actually, as seen below, it is possible to modulate agonistic/antagonistic activity of an antibody by modifying the structure of said antibody. For the first time, inventors report an original way to modulate such agonistic/antagonistic activity while conserving a divalent form for the antibody, aiming the conservation of good properties such as long half-life or effector functions.

It can also be mentioned here that, if the modification of the hinge region of a monoclonal antibody in order to increase the effector functions has already been reported in the prior art, it has never been reported, at the contrary, that such a modification into the hinge region could be of interest in the modulation of the agonistic/antagonistic activity of a monoclonal antibody. This is clearly the subject of the present invention which is novel and inventive regarding the existing prior art.

As an aspect in accordance with the process of the invention, the monoclonal antibody is a chimeric antibody.

By "chimeric" antibody, it is intended to indicate an antibody which contains a natural variable (light chain and heavy chain) region derived from an antibody of a given species in combination with the light chain and heavy chain constant regions of an antibody of a species heterologous to said given species (e.g. mouse, horse, rabbit, dog, cow, chicken, etc.).

The antibodies or their fragments of chimeric type according to the invention can be prepared by using the techniques of genetic recombination. For example, the chimeric antibody can be produced by cloning a recombinant DNA containing a promoter and a sequence coding for the variable region of a non-human, especially murine, monoclonal antibody according to the invention and a sequence coding for the constant region of human antibody. A chimeric antibody of the invention encoded by such a recombinant gene will be, for example, a mouse-man chimera, the specificity of this antibody being determined by the variable region derived from the murine DNA and its isotype determined by the constant region derived from the human DNA. For the methods of preparation of chimeric antibodies, it is possible, for example, to refer to the documents Verhoeyn et al. (BioEssays, 8:74, 1988), Morrison et al. (Proc. Natl. Acad. Sci. USA 82:6851-6855, 1984) or U.S. Pat. No. 4,816,567.

As another aspect in accordance with the process of the invention, the monoclonal antibody is a humanized antibody.

By "humanized antibody", it is intended to indicate an antibody which contains CDR regions derived from an antibody of non-human origin, the other parts of the antibody molecule being derived from one (or from several) human antibodies or germline sequences. Moreover, some of the residues of the segments of the skeleton (called FR) can be modified in order to conserve the affinity of the binding (Jones et al., Nature, 321:522-525, 1986; Verhoeyen et al., Science, 239:1534-1536, 1988; Riechmann et al., Nature, 332:323-327, 1988).

The humanized antibodies according to the invention or their fragments can be prepared by techniques known to the person skilled in the art (such as, for example, those described in the documents Singer et al., J. Immun. 150: 2844-2857, 1992; Mountain et al., Biotechnol. Genet. Eng. Rev., 10: 1-142, 1992; or Bebbington et al., Bio/Technology, 10:169-175, 1992).

Other humanization method are known by the man skill in the art as, for example, the "CDR Grafting" method described by Protein Design Lab (PDL) in the patent applications EP 0 451 216, EP 0 682 040, EP 0 939 127, EP 0 566 647 or U.S. Pat. No. 5,530,101, U.S. Pat. No. 6,180,370, U.S. Pat. No. 5,585,089 and U.S. Pat. No. 5,693,761. The following patent applications can also be mentioned: U.S. Pat. No. 5,639,641; U.S. Pat. No. 6,054,297; U.S. Pat. No. 5,886,152 and U.S. Pat. No. 5,877,293.

As another aspect in accordance with the process of the invention, the monoclonal antibody is a human antibody.

The term "human antibody" includes all antibodies that have one or more variable and constant region derived from human immunoglobulin sequences. In a preferred embodiment, all of the variable and constant domains (or regions) are derived from human immunoglobulin sequence (fully human antibody). In other words, it includes any antibody which has variable and constant regions (if present) derived from human germline immunoglobulin sequences, i.e. which possesses an amino acid sequence which corresponds to that of an antibody produced by a human and/or has been made using any techniques for making human antibodies known by the man skilled in the art.

In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As example for such transgenic mouse, it can be mentioned the XENOMOUSE™ which is an engineered mouse strain that comprises large fragments of the human immunoglobulin loci and is deficient in mouse antibody production (Green at al., 1994, Nature Genetics, 7:13-21). The XENOMOUSE™ produces an adult-like human repertoire of fully human antibodies, and generate antigen-specific human monoclonal antibodies. A second generation XENOMOUSE™ contains approximately 80% of the human antibody repertoire (Green & Jakobovits, 1998, J. Exp. Med., 188:483-495).

Any other technique known by the man skill in the art, such as phage display technique, can also be used for the generation of human antibody according to the invention.

The process according to the invention can be used for any type of immunoglobulin comprising a hinge region, i.e. IgA, IgD and IgG.

As an example, for the IgA isotype, the hinge region of an IgA1 comprises the amino acid sequence PSTPPTPSPST-PPTPSPS (SEQ ID No. 8) and the hinge region of an IgA2 comprises the amino acid sequence PPPPP (SEQ ID No. 9).

In a similar manner, the hinge region of an IgD comprises the amino acid sequence SPKAQASSVPTAQPQAEG-SLAKATTAPATTRNTRGGEEKKKEKEKEE QEERET-KTP (SEQ ID No. 10).

As a particular embodiment of the invention, it is preferred to use of an IgG including, for example, IgG1, IgG2, IgG3 or IgG4.

The respective amino acid sequences corresponding to the different isotypes of IgG hinge regions are:

```
                                          (SEQ ID No. 11)
PKSCDKTHTCPPCP
for an IgG1, (SEQ ID No. 7)
RKCCVECPPCP
for an IgG2, (SEQ ID No. 12)
LKTPLFTGDTTHTCPRCPEPKSCDTPPPCPRCPEPKSCDTPPPCPRCPEP KSCDTPPPCPRCP
for an IgG3,
and (SEQ ID No. 13)
SKYGPPCPSCP
for an IgG4.
```

Still more particularly, it is preferred to use an IgG1. Actually, in the field of therapeutical antibodies, and more particularly in the treatment of cancers, it is preferred to generate IgG1 to get effector functions such as ADCC and CDC in addition to functions linked to the specific binding to the targeted antigen.

The process of the invention is characterized in that said monoclonal antibody is an IgG1.

"Target molecule", within the meaning of the invention, relates to any molecule to which the monoclonal antibody is able to bind specifically or to modulate the activity. Generally, such target molecule can be named "antigen".

As non limitative example of target molecule which can be targeted by a monoclonal antibody, can be mentioned soluble ligands, receptors such as transmembrane receptors, membrane tumoral markers, etc.

In a preferred embodiment, said target molecule is a transmembrane receptor.

The expression "transmembrane receptor" relates to a protein that spans the plasma membrane of a cell, with the extracellular domain of the protein having the ability to bind to a ligand and the intracellular domain having an activity (such as a protein kinase) that can be altered (either increased or decreased) upon ligand binding. In other words, Transmembrane receptors are integral membrane proteins, which reside and operate typically within a cell's plasma membrane, but also in the membranes of some subcellular compartments and organelles. Binding to a signalling molecule or sometimes to a pair of such molecules on one side of the membrane, transmembrane receptors initiate a response on the other side. In this way they play a unique and important role in cellular communications and signal transduction.

Many transmembrane receptors are composed of two or more protein subunits which operate collectively and may dissociate when ligands bind, fall off, or at another stage of their "activation" cycles. They are often classified based on their molecular structure, or because the structure is unknown in any detail for all but a few receptors, based on their hypothesized (and sometimes experimentally verified) membrane topology. The polypeptide chains of the simplest are predicted to cross the lipid bilayer only once, while others cross as many as seven times (the so-called G-protein coupled receptors or GPCRs) or more.

Like any integral membrane protein, a transmembrane receptor may be subdivided into three parts or domains, an extracellular domain, a transmembrane domain and an intracellular domain.

The extracellular domain is the part of the receptor that sticks out of the membrane on the outside of the cell or organelle. If the polypeptide chain of the receptor crosses the bilayer several times, the external domain can comprise several "loops" sticking out of the membrane. By definition, a receptor's main function is to recognize and respond to a specific ligand, for example, a neurotransmitter or hormone (although certain receptors respond also to changes in transmembrane potential), and in many receptors these ligands bind to the extracellular domain.

In the majority of receptors for which structural evidence exists, transmembrane alpha helices make up most of the transmembrane domain. In certain receptors, such as the nicotinic acetylcholine receptor, the transmembrane domain forms a protein-lined pore through the membrane, or ion channel. Upon activation of an extracellular domain by binding of the appropriate ligand, the pore becomes accessible to ions, which then pass through. In other receptors, the transmembrane domains are presumed to undergo a conformational change upon binding, which exerts an effect intracellularly. In some receptors, such as members of the 7TM superfamily, the transmembrane domain may contain the ligand binding pocket.

The intracellular (or cytoplasmic) domain of the receptor interacts with the interior of the cell or organelle, relaying the signal. There are two fundamentally different ways for this interaction a) The intracellular domain communicates via specific protein-protein-interactions with effector proteins, which in turn send the signal along a signal chain to its destination and b) with enzyme-linked receptors, the intracellular domain has enzymatic activity. Often, this is a tyrosine kinase activity. The enzymatic activity can also be located on an enzyme associated with the intracellular domain.

There are several ways for the cell to regulate the activity of a transmembrane receptor. Most of them work through the intracellular domain. The most important ways are phosphorylation and internalization (see ubiquitin) or activation of second messenger cascades such as cAMP, IP, $Ca^{2+}$ or cGMP.

All membrane proteins showing enzymatic activities can also be targeted by antibodies with the modification described in this invention. Can be mentioned as examples, but without limitations, the matrix metalloprotease (MMP) family, the 'a disintegrin and a metalloprotease domain protease' (ADAM) family, adenylate cyclases, . . . .

All membrane proteins acting as ion channels, pores and transporters can also be targeted by antibodies with the modification described in this invention. Can be mentioned as examples, but without limitations, the sodium channel family, the potassium channel family, the nicotinic acetylcholine receptor family, the sigma receptors, the monoamine transporter family.

More broadly, all membrane proteins identified as specific markers for a given disease can also be targeted by an antibody treatment, which antibody can as well be improved by the modifications described in this invention.

In a preferred embodiment of the invention, said transmembrane receptor is selected from the group consisting of the tyrosine kinase receptor, tetraspanin and GPCRs.

In a more preferred embodiment, said transmembrane receptor is a tyrosine kinase receptor selected preferentially in the group consisting of IGF-1R, c-Met, RON, Axl, VEGF, VEGFR, Her-2neu, homodimers and heterodimers of the ErbB family, etc.

In the present application, and more particularly in the following specification, sequences will be defined in reference to IMGT. The IMGT unique numbering has been defined to compare the variable domains whatever the antigen receptor, the chain type, or the species [Lefranc M.-P., Immunology Today 18, 509 (1997); Lefranc M.-P., The Immunologist, 7, 132-136 (1999); Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002); Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

For the man skilled in the art, it will be obvious to transpose the invention described according the IMGT system into any other numbering system such as, for example, the Kabat numbering system.

The IMGT unique numbering for all IG and TR V-REGIONs of all species relies on the high conservation of the structure of the variable region. This numbering, set up after aligning more than 5000 sequences, takes into account and combines the definition of the framework (FR) and complementarity determining regions (CDR), structural data from X-ray diffraction studies, and the characterization of the hypervariable loops. The delimitations of the FR-IMGT and CDR-IMGT regions have been defined. Similarly, the IMGT unique numbering has been applied for the C-DOMAIN, and allows for precise delimitation of Ig-like domains. The C-DOMAIN corresponds to the complete C-REGION, to most of the C-REGION or to only part of the C-REGION, depending on the immunoglobulin (IG) type.

The IMGT numbering for C-DOMAIN (IG and TR) is derived as the IMGT unique numbering for V-DOMAIN, from the princeps IMGT unique numbering for V-REGION, up to position 104. Amino acid positions can therefore be easily compared between the C-DOMAIN and the V-DOMAIN.

To precisely locate the Hinge regions, the IMGT numbering of C-DOMAIN was applied to precisely locate CH1 and CH2 domains. The Hinge region includes all amino acid residues in between the last residue of IMGT-CH1 and the first residue of IMGT-CH2.

All other immunoglobulin numbering schemes such as Kabat or A. Honegger, covering the same Hinge domain are included in the present invention.

As a preferred example of the invention, based on the IMGT numbering system as above described, the amino acids sequence of the hinge region of an IgG1 comprises the residues H1 to H14 with the segment H1 to H9 corresponding to the Upper Hinge and the segment H10 to H14 corresponding to the Core Hinge. More particular, the human IgG1 hinge region comprises the amino acid sequence PKSCDKTHTCPPCP (SEQ ID No. 11) and the murine IgG1 hinge region comprises the amino acid sequence PRDCGCKPCICT (SEQ ID No. 14).

TABLE 1

| Hinge region | numbering | Hu-IgG1 (SEQ ID No. 11) | Mu-IgG1 (SEQ ID No. 14) | Hu-IgG2 (SEQ ID No. 7) | Hu-IgG4 (SEQ ID No. 11) |
|---|---|---|---|---|---|
| Upper Hinge | H1 | P | P | — | — |
| | H2 | K | R | R | S |
| | H3 | S | D | K | K |
| | H4 | C | C | C | Y |
| | H5 | D | G | — | — |
| | H6 | K | — | — | — |
| | H7 | T | C | C | G |
| | H8 | H | K | V | P |
| | H9 | T | P | E | P |
| Core Hinge | H10 | C | C | C | C |
| | H11 | P | I | P | P |
| | H12 | P | — | P | S |
| | H13 | C | C | C | C |
| | H14 | P | T | P | P |

In a preferred embodiment of the invention, it is considered a modification aiming at reducing the length of the protein sequence coding for the hinge region of a divalent antibody. More particularly, the process according to the invention comprises a step of deletion of at least one amino acid in the hinge region.

As previously mentioned, it is preferred the deletion of at most 2 amino acids of said hinge region.

As previously mentioned, it is preferred the deletion of at most 3 amino acids of said hinge region.

As previously mentioned, it is preferred the deletion of at most 4 amino acids of said hinge region.

In a particular use of the process of the invention, the modification consists of at least a deletion of an amino acid selected from the amino acid in position H1, H2, H3, H5, H6, H7, H8, H9, H11, H12 or H14.

More particularly, inventors have demonstrated the implication of particular residue and a particular inventive aspect of the invention consists of the selection of certain residues.

In the preferred case of an IgG1, the amino acid in position H1 consists of a Proline; the amino acid in position H2 consists of a Lysine in the human version and of a Arginine in the murine version; the amino acid in position H3 consists of a Serine in the human version and of a Aspartate in the murine version; the amino acid in position H5 consists of an aspartate in the human version and of a Glycine in the murine version; the amino acid in position H6 consists of a Lysine; the amino acid in position H8 consists of a Histidine in the human version and of a Lysine in the murine version; the amino acid in position H9 consists of a Threonine in the human version and of a Proline in the murine version; the amino acid in position H11 consists of a Proline in the human version and of a Isoleucine in the murine version; and the amino acid in position H12 consists of a Proline in the human version.

According to a preferred embodiment, this deletion has to be done in the "upper hinge" region.

In a more preferred embodiment, this deletion is part of the "upper hinge" constituted, for an IgG1 for example, of the amino acids H1 to H9 by comparison to the "Core hinge" constituted of the amino acids H10 to H14.

In the present application, the amino acid numbering is done regarding the IMGT system as previously described. It is obvious that any other numbering system, with a modification of the numbering but not the nature of residue implicated in the hinge region, must be considered as equivalent. As an example, renumbering the identified amino acid part of the invention (according to the IMGT system) in the Kabat system must be considered as equivalent.

Another aspect of the invention is based on the deletion of at least one Cysteine into the "upper hinge" region, preferably located in the position H4.

Another aspect of the invention is based on the addition of at least one disulfide bridge into the hinge region.

More particularly, the process of the invention is characterized in that the modification consists of the introduction of at least one Cysteine into the "upper hinge" region.

According to the inventors, a plausible explanation is based on a possible "rigidifcation" of the hinge resulting from either the reduction of the length and/or the introduction of another disulfide bridge. Such a "rigidification" will allow to maintain a appropriate spatial conformation of the antibody with, as a consequence, an improved antagonistic activity.

It is clear that any method aiming at rigidifying the hinge region must be considered as an equivalent method to the process according to the present invention.

The introduction of a Cysteine can be done by addition of such an amino acid, said addition being done by any method known by the man skilled in the art.

Another preferred way to introduce a Cysteine into the hinge region consists of a substitution of at least an amino acid.

More particularly, a preferred way to introduce a Cysteine into the hinge region consists of a substitution of at least an amino acid selected from H1 to H9. Such a substitution can be done by any method known by the skilled artisan.

More particularly, the process of the invention comprises the substitution of the Threonine in position H7 into the "upper hinge" region by a Cysteine.

In another embodiment, the process of the invention comprises the substitution of the Lysine in position H6 into the "upper hinge" region by a Cysteine.

In still another embodiment, the process of the invention comprises the substitution of the Proline in position H1 into the "upper hinge" region by a Cysteine.

In still another embodiment, the process of the invention comprises the substitution of the Lysine in position H2 into the "upper hinge" region by a Cysteine.

In still another embodiment, the process of the invention comprises the substitution of the Serine in position H3 into the "upper hinge" region by a Cysteine.

In still another embodiment, the process of the invention comprises the substitution of the Aspartate in position H5 into the "upper hinge" region by a Cysteine.

In still another embodiment, the process of the invention comprises the substitution of the Histidine in position H8 into the "upper hinge" region by a Cysteine.

In still another embodiment, the process of the invention comprises the substitution of the Threonine in position H9 into the "upper hinge" region by a Cysteine.

According to another embodiment, it is also possible to reduce the length of the hinge region and/or to add a disulfide bridge by changing the whole of the amino acid sequence encoding for the hinge region.

As a preferred example, the modification of the process of the invention consists of a replacement of the amino acids H1 to H14 of the IgG1 hinge region by the amino acid H1 to H14 of an IgG2 hinge region, preferably when said monoclonal antibody which is desired to improve its antagonistic activity is an IgG1 antibody.

In another application, the invention relates to a process of screening for an antagonist monoclonal antibody directed against a specific target molecule, or a divalent functional fragment or derivative thereof, said antibody being capable of inhibiting one or more of the biological activities of said target molecule, wherein said process comprises the steps of:
  (a) selecting an initial antibody with an initial level of inhibition of said one or more biological activity of said target molecule,
  (b) modifying the amino acid sequence of the hinge region of said initial antibody by the process of the invention,
  (c) evaluating the modified antibody of step (b) for its ability to inhibit said one or more biological activity of said target molecule, and
  (d) selecting, as a positive result, the antibody of step (c) with an inhibition level of said one or more biological activity of said target molecule higher than the initial level of said inhibition.

Initial antibodies can be selected amongst the existing antibodies such as, without limitation, antibodies antagonists to IGF-1R, c-Met, RON, Axl, CD151, VEGF, VEGFR, Her-2neu, homodimers and heterodimers of the ErbB family. As non limitative preferred example, said initial antibodies can consist of Herceptin, Pertuzumab, Cetuximab, anti-VEGFR or anti-IGF-1R antibodies.

"Inhibition level", within the meaning of the invention, illustrates the antagonistic activity of an antibody. Such inhibition level can be determined by any method known by the skilled artisan such as, without limitation, such as a) direct cell counting or use of 3[H]Thymidine, tetrazoline salts or any other fluorescent mean to evaluate proliferation, b) western blotting, phospho-ELISA or alpha-screen assays to monitor signal transduction, c) BRET or FRET analysis for dimerization assay, d) microscopy or fluorescent methods to monitor migration, invasion, angiogenesis or morphogenesis and e) calliper measurement of tumors for in vivo evaluations.

This screening process can be used for the improvement of validated antibodies or as a selection stage for research or pre-clinical antibodies.

Another aspect in accordance with the invention relates to a monoclonal antibody directed against a specific target molecule, or divalent functional fragments or derivatives thereof, obtainable by the process of the invention, said antibody being characterized in that it comprises a hinge region amino acid sequence selected from the group consisting of SEQ ID No. 1 (PRDCGCKPCICT), SEQ ID No. 2 (PKSCGCKPCICT), SEQ ID No. 3 (PKSCGCKPCICP), SEQ ID No. 4 (PRDCGCKPCPPCP), SEQ ID No. 5 (PRDCGCHTCPPCP), SEQ ID No. 6 (PKSCDCHCPPCP), SEQ ID No. 7 (RKCCVECPPCP), SEQ ID No. 22 (CKSCDKTHTCPPCP), SEQ ID No. 23 (PCSCDKTHTCPPCP), SEQ ID No. 24 (PKCCDKTHTCPPCP), SEQ ID No. 25 (PKSCCKTHTCPPCP), SEQ ID No. 26 (PKSCDCTHTCPPCP) SEQ ID No. 27 (PKSCDKCHTCPPCP), SEQ ID No. 28 (PKSCDKTCTCPPCP), SEQ ID No. 29 (PKSCDKTHCCPPCP), SEQ ID No. 30 (PKSCDKTHTCCPCP), SEQ ID No. 31 (PKSCDKTHTCPCCP), SEQ ID No. 32 (PKSCDKTHTCPPCC), SEQ ID No. 33 (PSCDKTHTCPPCP), SEQ ID No. 34 (PKSCDTHTCPPCP), SEQ ID No. 35 (PKSCDKTHCPPCP), SEQ ID No. 36 (KCDKTHTCPPCP), SEQ ID No. 37 (PSCKTHTCPPCP), SEQ ID No. 38 (PKSCDTHCPPCP), SEQ ID No. 39 (PKSCTHTCPPCP), SEQ ID No. 40 (PKSCDKTTCPCP), SEQ ID No. 41 (PKSCDKTHCPPC), SEQ ID No. 42 (PKSCDCHTCPPCP), SEQ ID No. 43 (PKSCDCTHCPPCP), SEQ ID No. 44 (PCSCKHTCPPCP), SEQ ID No. 45 (PSCCTHTCPPCP), SEQ ID No. 46 (PSCDKHCCPPCP), SEQ ID No. 47 (PKSTHTCPPCP), SEQ ID No. 48 (PKSCTCPPCP) or SEQ ID No. 49 (PKSCDKCVECPPCP).

A preferred monoclonal antibody obtained by the implementation of the process of the invention can be characterized in that it comprises an amino acid sequence selected from the group consisting of SEQ ID No. 1 (PRDCGCKPCICT), SEQ ID No. 2 (PKSCGCKPCICT), SEQ ID No. 3 (PKSCGCKPCICP), SEQ ID No. 4 (PRDCGCKPCPPCP), SEQ ID No. 5 (PRDCGCHTCPPCP), SEQ ID No. 6 (PKSCDCHCPPCP), SEQ ID No. 7 (RKCCVECPPCP), SEQ ID No. 22 (CKSCDKTHTCPPCP), SEQ ID No. 23 (PCSCDKTHTCPPCP), SEQ ID No. 24 (PKCCDKTHTCPPCP), SEQ ID No. 25 (PKSCCKTHTCPPCP), SEQ ID No. 26 (PKSCDCTHTCPPCP) SEQ ID No. 27 (PKSCDKCHTCPPCP), SEQ ID No. 28 (PKSCDKTCTCPPCP), SEQ ID No. 29 (PKSCDKTHCCPPCP), SEQ ID No. 30 (PKSCDKTHTCCPCP), SEQ ID No. 31 (PKSCDKTHTCPCCP), SEQ ID No. 32 (PKSCDKTHTCPPCC), SEQ ID No. 33 (PSCDKTHTCPPCP), SEQ ID No. 34 (PKSCDTHTCPPCP), SEQ ID No. 35 (PKSCDKTHCPPCP), SEQ ID No. 36 (KCDKTHTCPPCP), SEQ ID No. 37 (PSCKTHTCPPCP), SEQ ID No. 38 (PKSCDTHCPPCP), SEQ ID No. 39 (PKSCTHTCPPCP), SEQ ID No. 40 (PKSCDKTTCPCP), SEQ ID No. 41 (PKSCDKTHCPPC), SEQ ID No. 42 (PKSCDCHTCPPCP), SEQ ID No. 43 (PKSCDCTHCPPCP), SEQ ID No. 44 (PCSCKHTCPPCP), SEQ ID No. 45 (PSCCTHTCPPCP), SEQ ID No. 46 (PSCDKHCCPPCP), SEQ ID No. 47 (PKSTHTCPPCP), SEQ ID No. 48 (PKSCTCPPCP) or SEQ ID No. 49 (PKSCDKCVECPPCP).

In a preferred embodiment, said monoclonal antibody is a human antibody, more preferred is an IgG1 antibody.

The invention also relates to an isolated nucleic acid encoding for a monoclonal antibody as previously described, i.e. comprising a hinge region amino acid sequence selected from the group consisting of SEQ ID No. 1 (PRDCGCKPCICT), SEQ ID No. 2 (PKSCGCKPCICT), SEQ ID No. 3 (PKSCGCKPCICP), SEQ ID No. 4 (PRDCGCKPCPPCP), SEQ ID No. 5 (PRDCGCHTCPPCP), SEQ ID No. 6 (PKSCDCHCPPCP), SEQ ID No. 7 (RKCCVECPPCP), SEQ ID No. 22 (CKSCDKTHTCPPCP), SEQ ID No. 23 (PCSCDKTHTCPPCP), SEQ ID No. 24 (PKCCDKTHTCPPCP), SEQ ID No. 25 (PKSCCKTHTCPPCP), SEQ ID No. 26 (PKSCDCTHTCPPCP) SEQ ID No. 27 (PKSCDKCHTCPPCP), SEQ ID No. 28 (PKSCDKTCTCPPCP), SEQ ID No. 29 (PKSCDKTHCCPPCP), SEQ ID No. 30 (PKSCDKTHTCCPCP), SEQ ID No. 31 (PKSCDKTHTCPCCP), SEQ ID No. 32 (PKSCDKTHTCPPCC), SEQ ID No. 33 (PSCDKTHTCPPCP), SEQ ID No. 34 (PKSCDTHTCPPCP), SEQ ID No. 35 (PKSCDKTHCPPCP), SEQ ID No. 36 (KCDKTHTCPPCP), SEQ ID No. 37 (PSCKTHTCPPCP), SEQ ID No. 38 (PKSCDTHCPPCP), SEQ ID No. 39 (PKSCTHTCPPCP), SEQ ID No. 40 (PKSCDKTTCPCP), SEQ ID No. 41 (PKSCDKTHCPPC), SEQ ID No. 42 (PKSCDCHTCPPCP), SEQ ID No. 43 (PKSCDCTHCPPCP), SEQ ID No. 44 (PCSCKHTCPPCP), SEQ ID No. 45 (PSCCTHTCPPCP), SEQ ID No. 46 (PSCDKHCCPPCP), SEQ ID No. 47 (PKSTHTCPPCP), SEQ ID No. 48 (PKSCTCPPCP) or SEQ ID No. 49 (PKSCDKCVECPPCP).

According to still another aspect, the present invention relates to an isolated nucleic acid, characterized in that it is chosen from the following nucleic acids:

a) a nucleic acid, DNA or RNA, coding for an artificial hinge region according to the invention, the corresponding RNA nucleic acid thereof or the complementary sequence thereof;

b) an isolated nucleic acid sequence comprising a nucleic sequence selected from the group consisting of SEQ ID No. 15 to SEQ ID No. 21, SEQ ID No. 50 to SEQ ID No. 77, the corresponding RNA nucleic acid thereof and the complementary sequence thereof; and c) a nucleic acid of at least 18 nucleotides capable of hybridizing under conditions of high stringency with at least one of the sequences SEQ ID Nos. 15 to 21 and 50 to 77.

Preferably, the invention comprises an isolated nucleic acid comprising a nucleic sequence selected from the group consisting of SEQ ID No. 15 to SEQ ID No. 21 and SEQ ID No. 50 to SEQ ID No. 77.

Also part of the invention is an expression vector or a transformed host cell comprising an isolated nucleic acid as previously described and, more particularly, an isolated nucleic acid comprising a nucleic sequence selected from the group consisting of SEQ ID No. 15 to SEQ ID No. 21 and SEQ ID No. 50 to SEQ ID No. 77, the corresponding RNA nucleic acid thereof and the complementary sequence thereof.

By nucleic acid, nucleic or nucleic acid sequence, polynucleotide, oligonucleotide, polynucleotide sequence, nucleotide sequence, terms which will be employed indifferently in the present invention, it is intended to indicate a precise linkage of nucleotides, which are modified or unmodified, allowing a fragment or a region of a nucleic acid to be defined, containing or not containing unnatural nucleotides, and being able to correspond just as well to a double-stranded DNA, a single-stranded DNA as to the transcription products of said DNAs.

It must also be understood here that the present invention does not concern the nucleotide sequences in their natural chromosomal environment, that is to say in the natural state. It concerns sequences which have been isolated and/or purified, that is to say that they have been selected directly or indirectly, for example by copy, their environment having been at least partially modified. It is thus likewise intended to indicate here the isolated nucleic acids obtained by genetic recombination by means, for example, of host cells or obtained by chemical synthesis.

A hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SDS), 10×Denhardt's, 5% of dextran sulfate and 1% of salmon sperm DNA; (2) actual hybridization for 20 hours at a temperature dependent on the size of the probe (i.e.: 42° C., for a probe size>100 nucleotides) followed by 2 washes of 20 minutes at 20° C. in 2×SSC+2% of SDS, 1 wash of 20 minutes at 20° C. in 0.1×SSC+0.1% of SDS. The last wash is carried out in 0.1×SSC+0.1% of SDS for 30 minutes at 60° C. for a probe size>100 nucleotides. The hybridization conditions of high stringency described above for a polynucleotide of defined size can be adapted by the person skilled in the art for oligonucleotides of greater or smaller size, according to the teaching of Sambrook et al. (1989, Molecular cloning: a laboratory manual. 2nd Ed. Cold Spring Harbor).

The invention likewise relates to a vector comprising a nucleic acid according to the present invention.

The invention aims especially at cloning and/or expression vectors which contain a nucleotide sequence according to the invention.

The vectors according to the invention preferably contain elements which allow the expression and/or the secretion of the translated nucleotide sequences in a determined host cell. The vector must therefore contain a promoter, signals of initiation and termination of translation, as well as appropriate regions of regulation of transcription. It must be able to be maintained in a stable manner in the host cell and can optionally have particular signals which specify the secretion of the translated protein. These different elements are chosen and optimized by the person skilled in the art as a function of the host cell used. To this effect, the nucleotide sequences according to the invention can be inserted into autonomous replication vectors in the chosen host, or be integrative vectors of the chosen host.

Such vectors are prepared by methods currently used by the person skilled in the art, and the resulting clones can be introduced into an appropriate host by standard methods, such as lipofection, electroporation, thermal shock, or chemical methods.

The vectors according to the invention are, for example, vectors of plasmidic or viral origin. They are useful for transforming host cells in order to clone or to express the nucleotide sequences according to the invention.

The invention likewise comprises the host cells transformed by or comprising a vector according to the invention.

The host cell can be chosen from prokaryotic or eukaryotic systems, for example bacterial cells but likewise yeast cells or animal cells, in particular mammalian cells. It is likewise possible to use insect cells or plant cells.

Figure 1B:
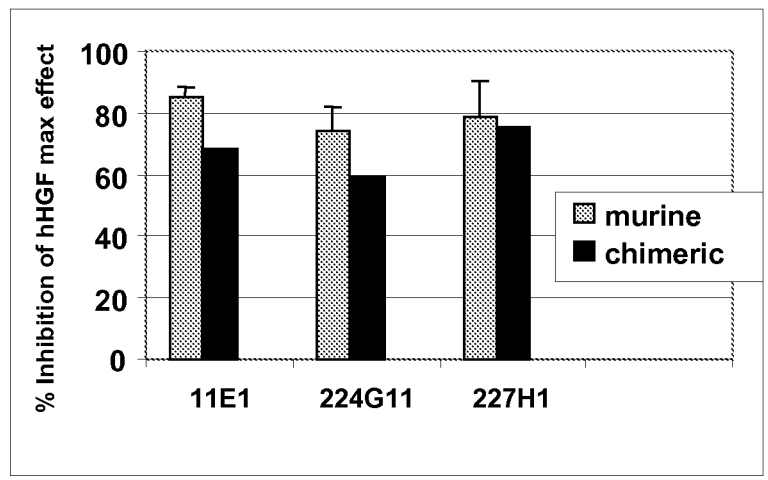

Other characteristics and advantages of the invention appear in the continuation of the description with the examples and the figures wherein:

FIGS. 1A and 1B: Effect a series of murine and corresponding chimeric anti-c-Met Mabs produced as a human IgG1/kappa isotype on c-Met receptor phosphorylation on A549 cells.

FIG. 1A: agonist effect calculated as percentage versus maximal stimulation of c-Met phosphorylation by HGF [100 ng/ml].

FIG. 1B: antagonist effect calculated as percentage of inhibition of the maximal stimulation of c-Met phosphorylation by HGF [100 ng/ml].

Figure 2A:
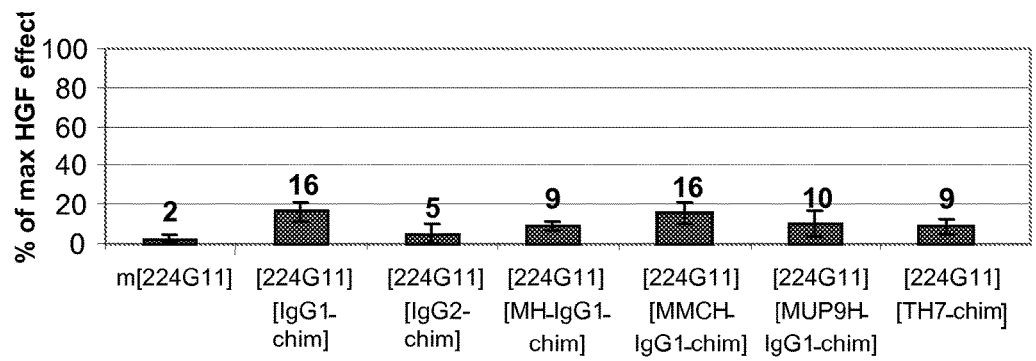
Figure 2B:
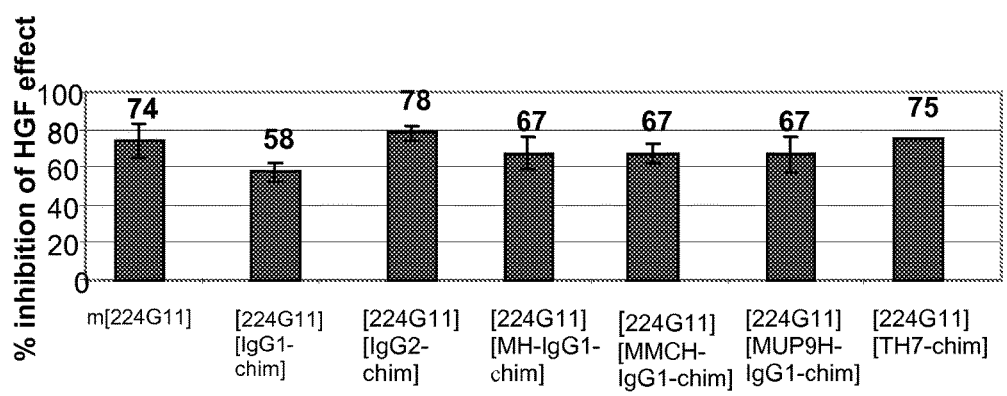
Figure 3A:
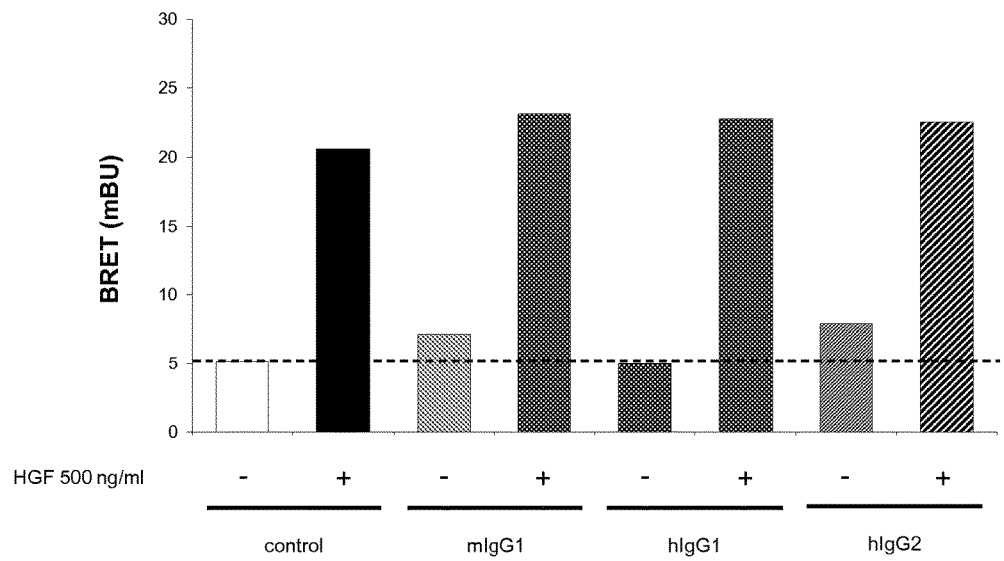
Figure 3B:
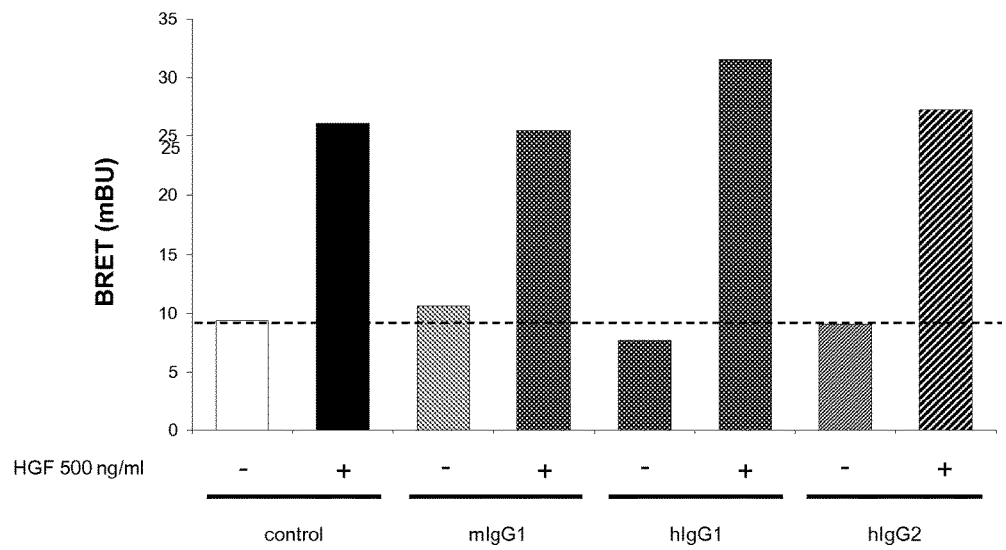
Figure 4:
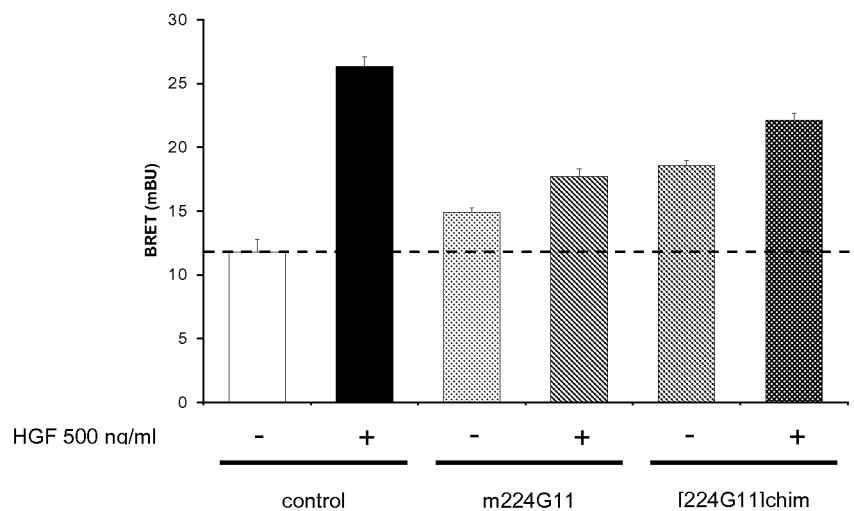

FIGS. 2A and 2B: Comparison between murine 224G11 Mab and chimeric 224G11 Mabs containing various engineered hinge regions, on c-Met receptor phosphorylation on A549 cells.

FIG. 2A: agonist effect calculated as percentage versus maximal stimulation of c-Met phosphorylation by HGF [100 ng/ml].

FIG. 2B: antagonist effect calculated as percentage of inhibition of the maximal stimulation of c-Met phosphorylation by HGF [100 ng/ml].

FIGS. 3A and 3B, 4 and 5: c-Met dimerization and activation BRET models.

Figure 6A:
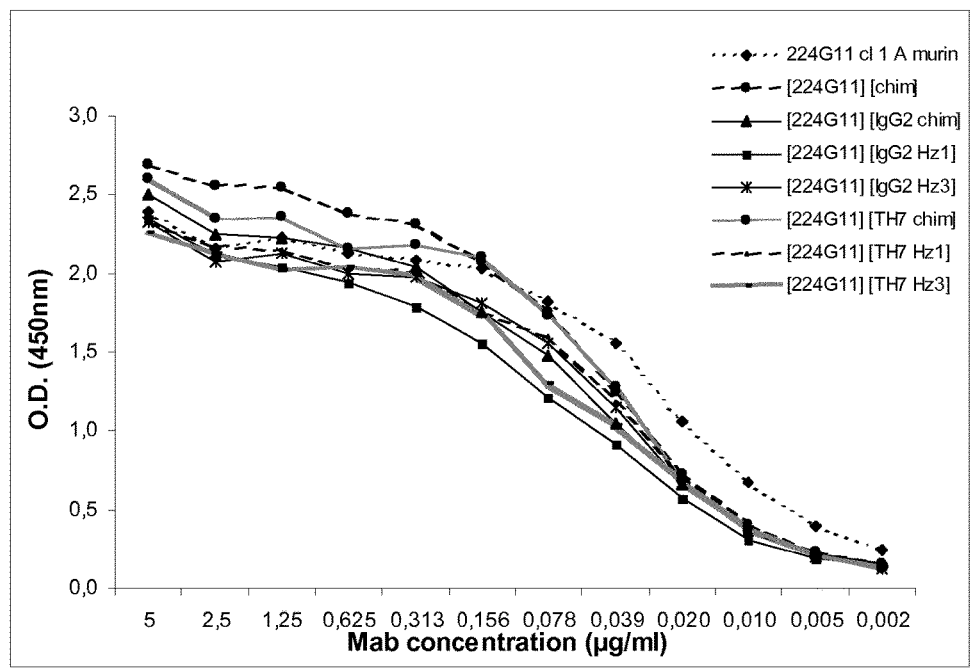
Figure 6B:
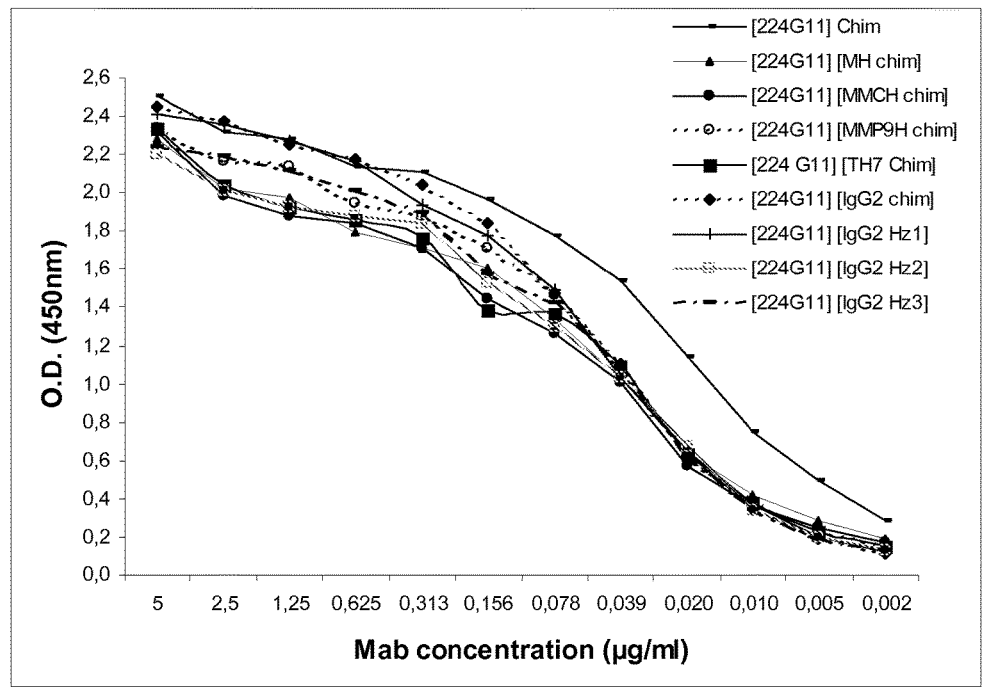

FIGS. 6A and 6B: c-Met recognition by chimeric and humanized 224G11 forms.

Figure 7A:
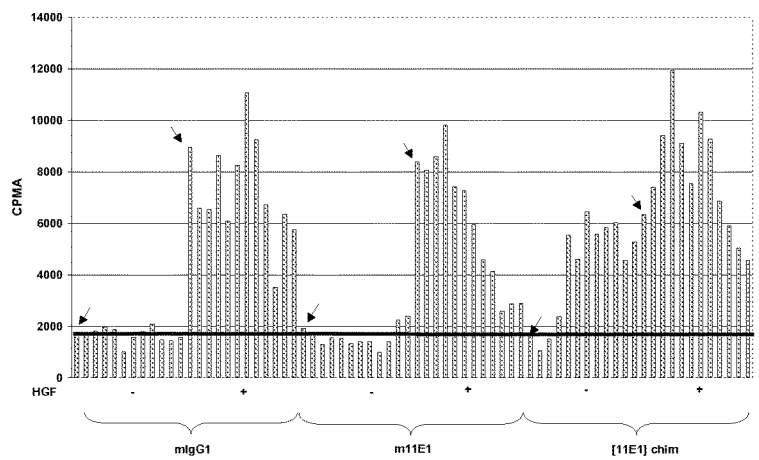
Figure 7B:
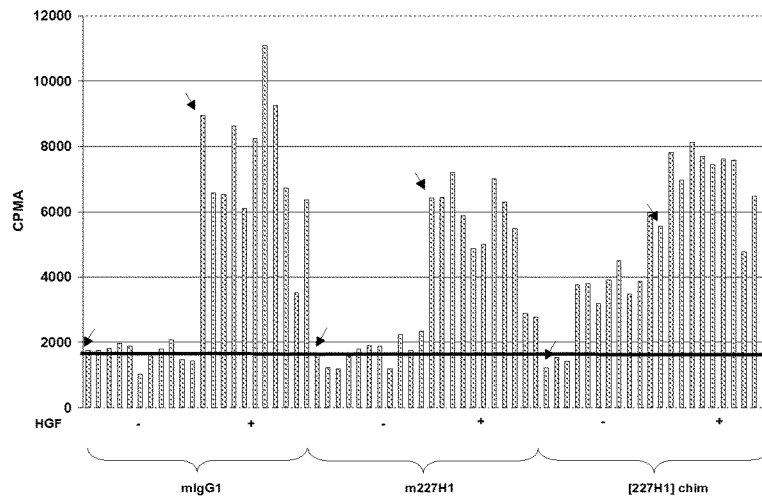
Figure 7C:
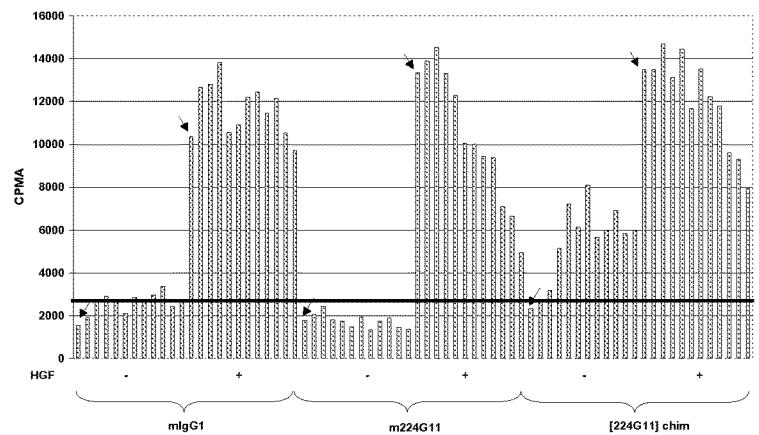

FIGS. 7A, 7B and 7C: Effect of murine and chimeric antibodies on HGF-induced proliferation of NCI-H441 cells in vitro. NCI-H441 cells were plated in serum-free medium. Twenty four hours after plating (FIG. 7A) m1E1 and [11E1] chim, (FIG. 7B) m227H1 and [227H1] chim or (FIG. 7C) m224G11 and [224G11] chim were added either in absence or in presence of HGF. Black arrows indicate the wells plated with cells alone either in absence ↙ or in presence ↘ of HGF. A murine IgG1 (mIgG1) was introduced as an isotype control.

Figure 8:
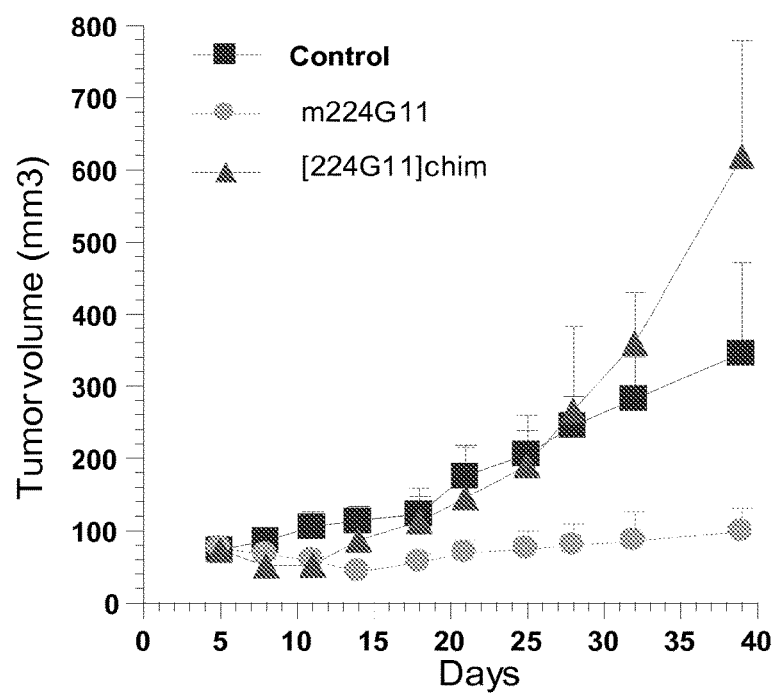

FIG. 8: In vivo comparison of murine and chimeric 224G11 Mabs on the NCI-H441 xenograft model.

Figure 9A:
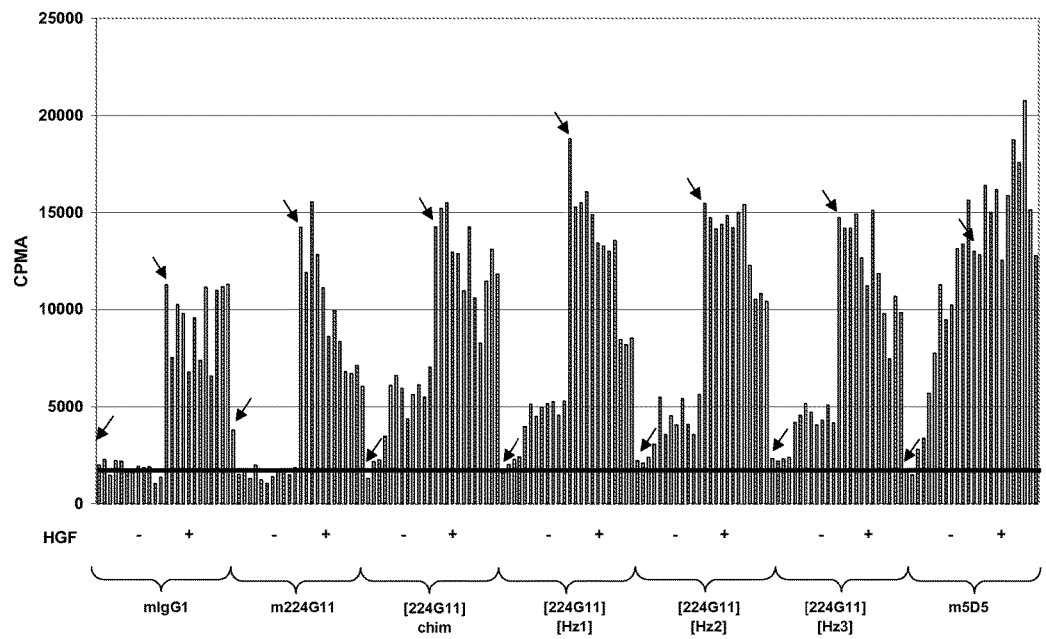
Figure 9B:
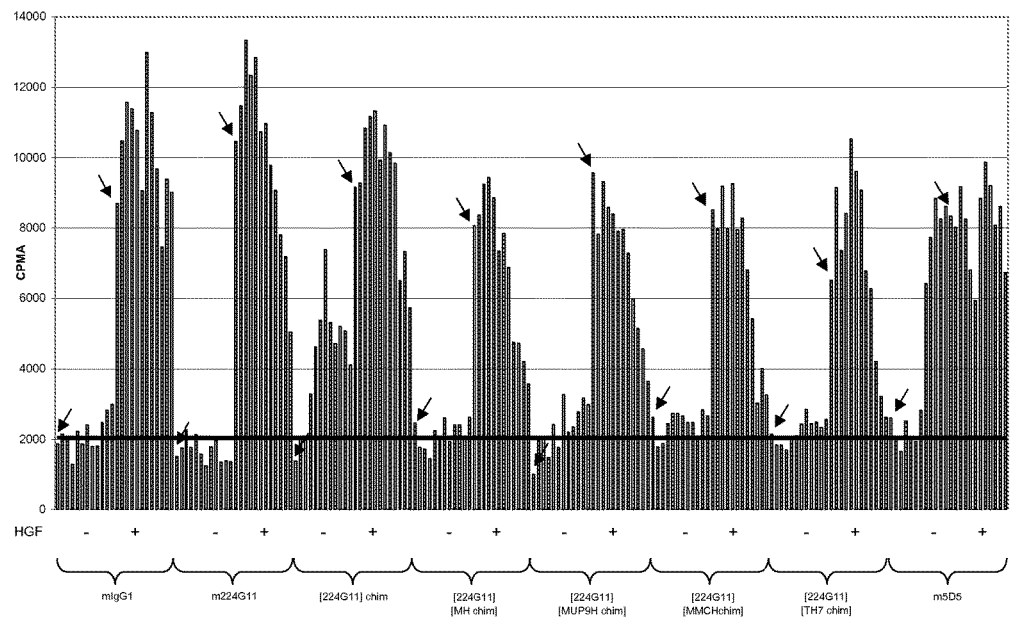

FIGS. 9A and 9B: Effect of the murine 224G11 Mab and of various chimeric and humanized versions of this antibody on HGF-induced proliferation of NCI-H441 cells in vitro. NCI-H441 cells were plated in serum-free medium. Twenty four hours after plating antibody to be tested were added either in absence or in presence of HGF. In panel (FIG. 9A), the murine m224G11, chimeric IgG1 [224G11] chim, humanized IgG1 [224G11] [Hz1], [224G11] [Hz2], [224G11] [Hz3] versions were shown. In panel (FIG. 9B), the murine m224G11 and various chimeric IgG1 forms ([224G11] chim, [224G11] [MH chim], [224G11] [MUP9H chim], [224G11] [MMCH chim], [224G11] [TH7 chim]) were presented. Black arrows indicate the wells plated with cells alone either in absence ↙ or in presence ↘ of HGF. A murine IgG1 was introduced as a negative control for agonist activity. The m5D5 was used as a dose-dependent full agonist control.

Figure 10:
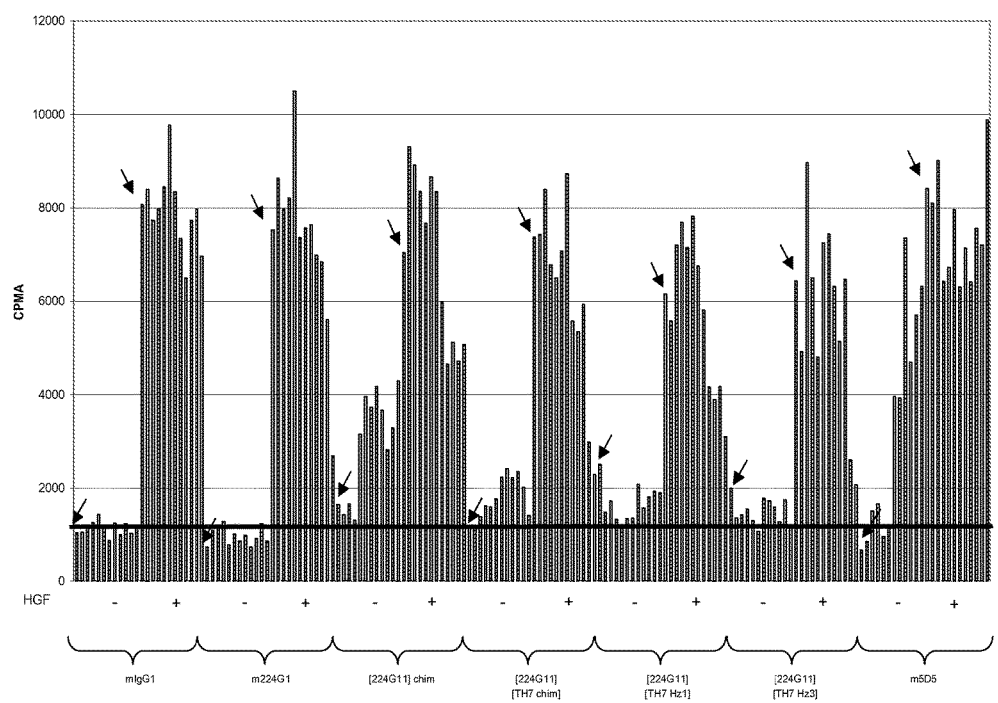

FIG. 10: Effect of the murine 224G11 Mab and of various chimeric and humanized versions of this antibody on HGF-induced proliferation of NCI-H441 cells in vitro. NCI-H441 cells were plated in serum-free medium. Twenty four hours after plating antibody to be tested were added either in absence or in presence of HGF. The murine m224G11, [224G11] chim, [224G11] [TH7 chim]) IgG1 chimeric forms and [224G11] [TH7 Hz1], [224G11] [TH7 Hz3]), were presented. Black arrows indicate the wells plated with cells alone either in absence ⬉ or in presence ⬊ of HGF. A murine IgG1 was introduced as a negative control for agonist activity. The m5D5 was used as a dose-dependent full agonist control.

FIGS. 11A-11B and 12A-12B: Effect a series of anti-c-Met Mabs, with engineered hinge, of the invention on c-Met receptor phosphorylation on A549 cells.

Figure 11A:
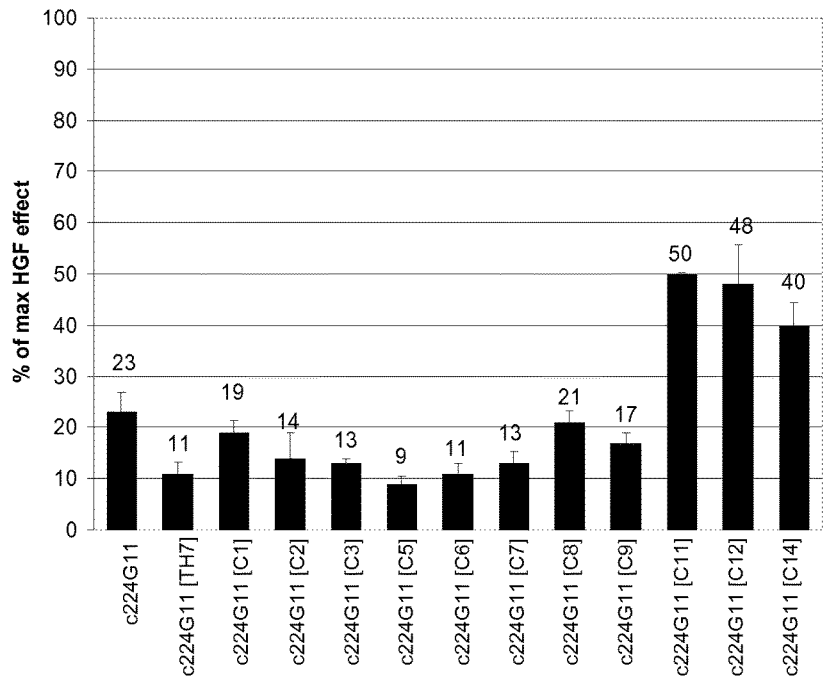
Figure 11B:
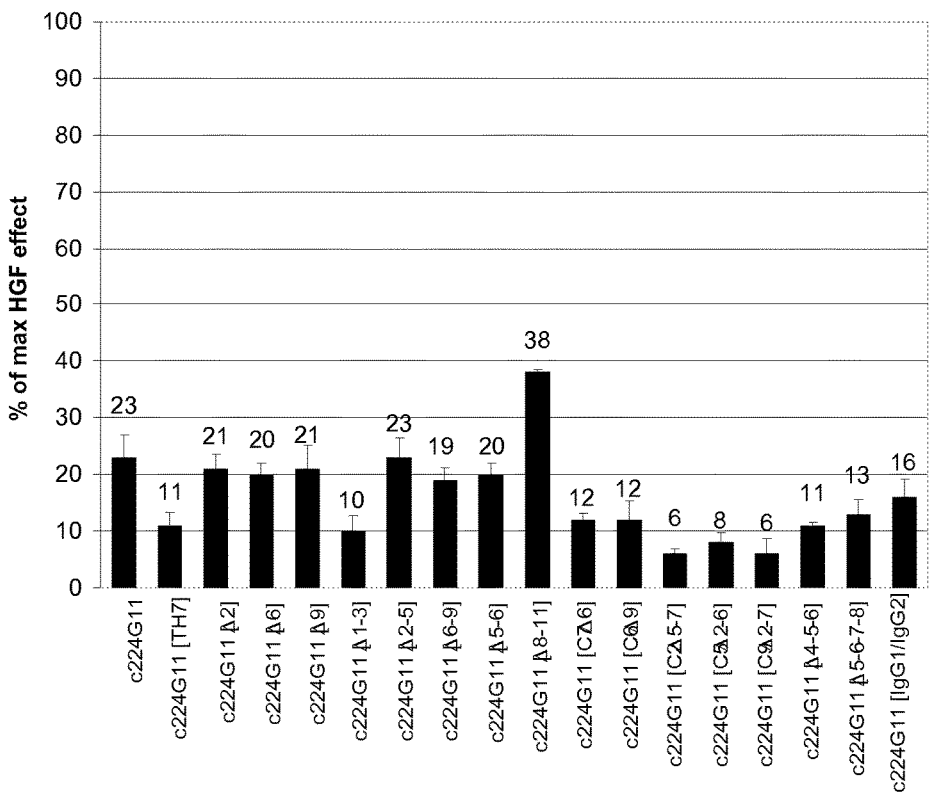

FIGS. 11A and 11B: agonist effect calculated as percentage versus maximal stimulation of c-Met phosphorylation by HGF [100 ng/ml].

Figure 12A:
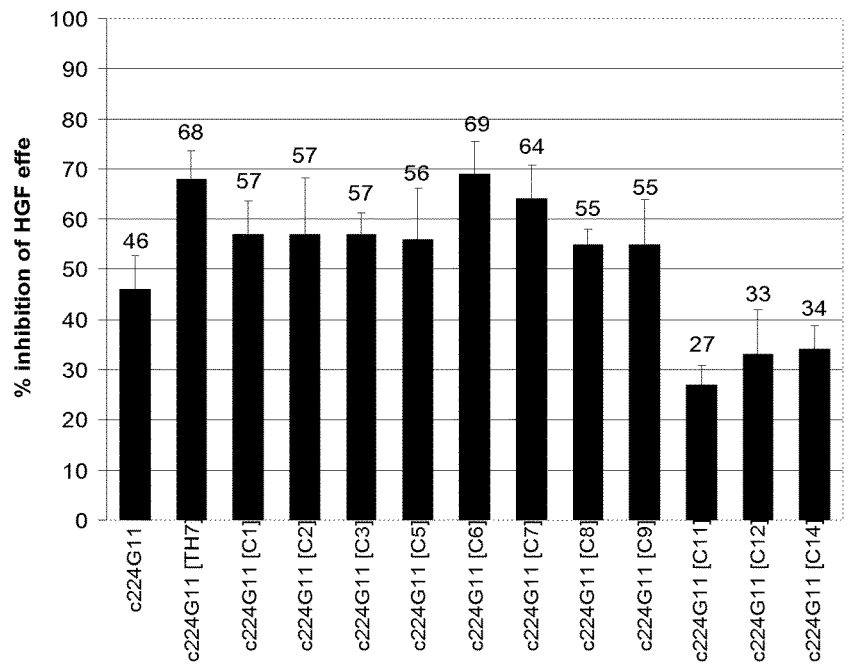
Figure 12B:
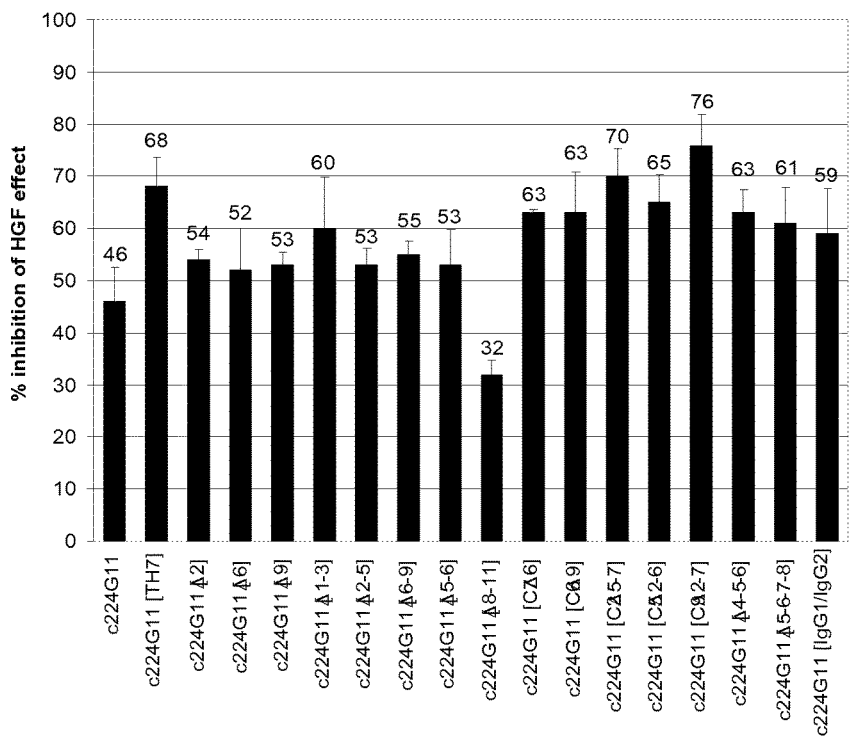

FIGS. 12A and 12B: antagonist effect calculated as percentage of inhibition of the maximal stimulation of c-Met phosphorylation by HGF [100 ng/ml].

Figure 13A:
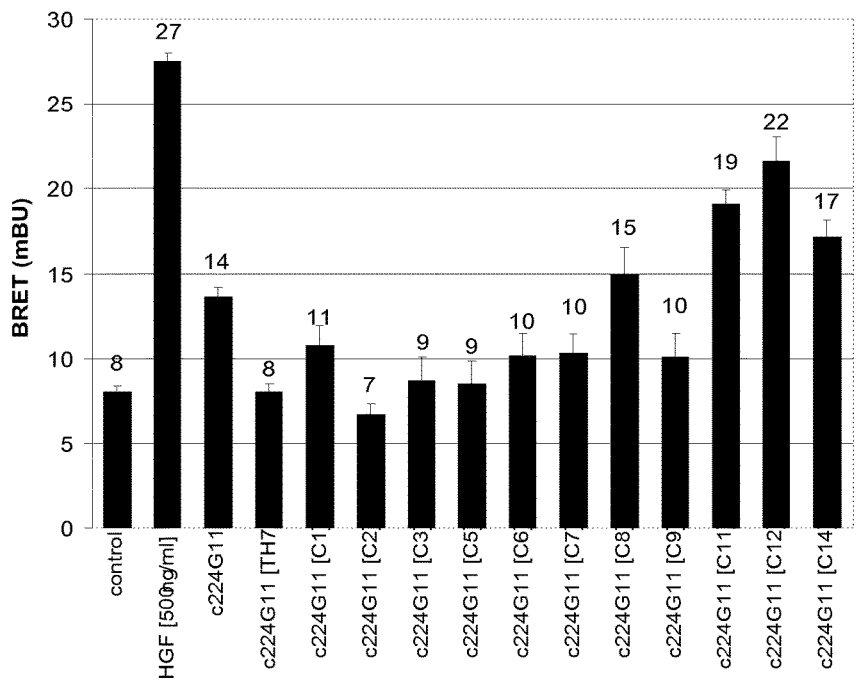
Figure 13B:
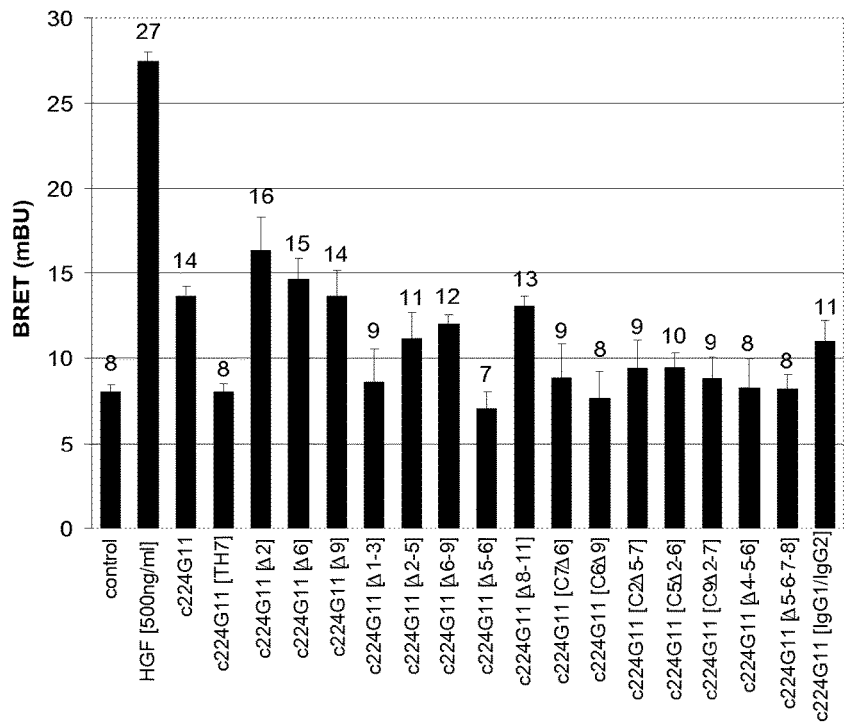

FIGS. 13A and 13B: c-Met dimerization and activation BRET models.

Figure 14A:
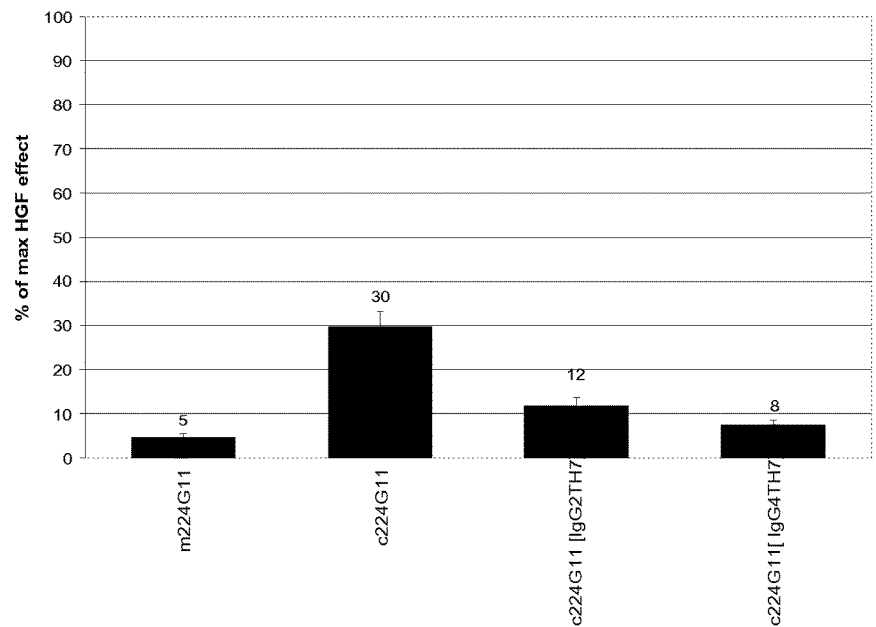

FIG. 14A: agonist effect calculated as percentage versus maximal stimulation of c-Met phosphorylation by HGF [100 ng/ml].

Figure 14B:
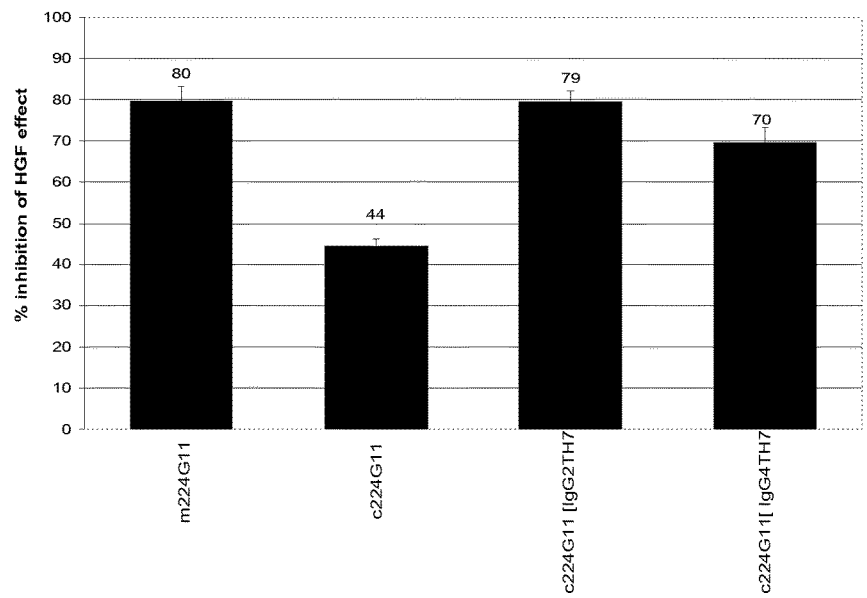

FIG. 14B: antagonist effect calculated as percentage of inhibition of the maximal stimulation of c-Met phosphorylation by HGF [100 ng/ml].

Figure 15:
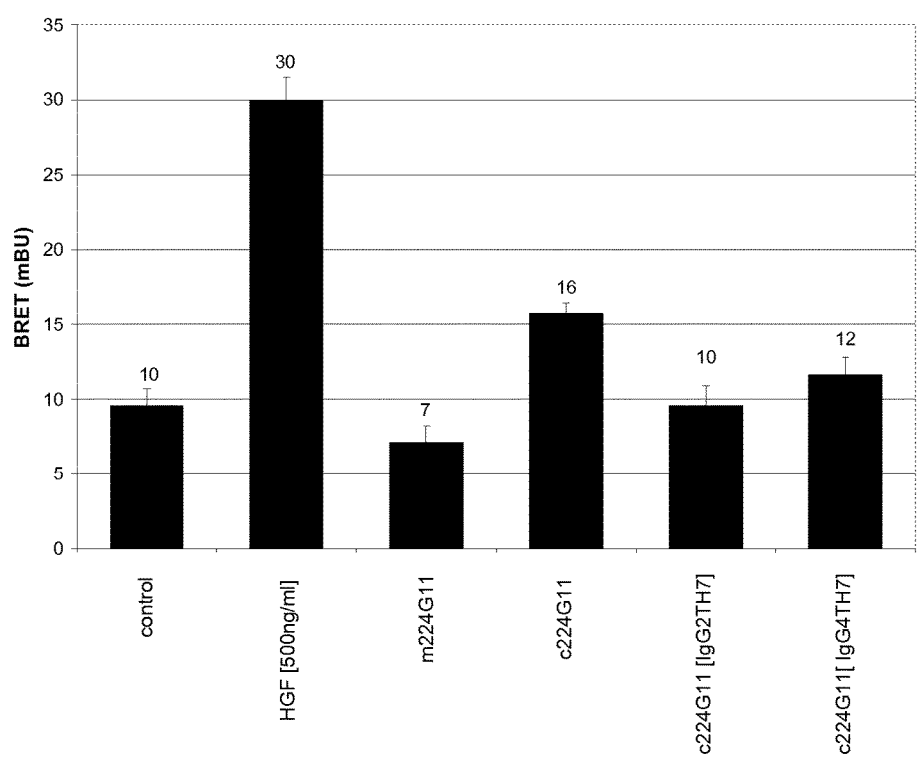

FIG. 15: c-Met dimerization and activation BRET models.

Figure 16:
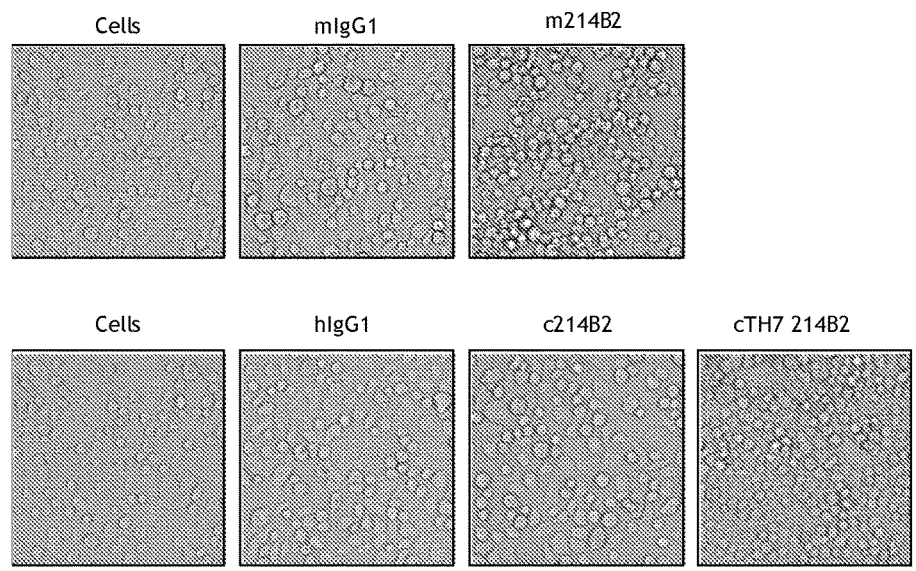

FIG. 16: Microscope analysis of the effect of different forms of Mab 214B2 on PC3 cell adhesion.

Figure 17:
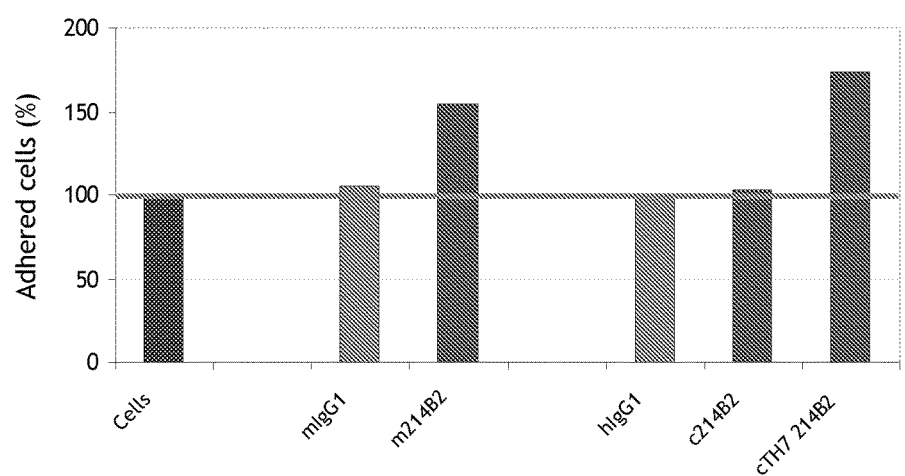

FIG. 17: Analysis of the effect of different forms of Mab 214B2 on PC3 cell adhesion using an ATP assay. In each well the number of adhered cells was determined using PC3 standard curve, from 0 to 200000 cells/well. The results are presented as follows: the untreated cells are taken as reference (100%) and the treated cells are presented as the % of reference.

EXAMPLE 1

Construction of Chimeric Mabs and Functional Evaluation of c-Met Receptor Phosphorylation Status Several mouse Mabs, targeting a prototypical tyrosine kinase receptor (c-Met receptor) were reformatted as chimeric Mabs carrying mouse variable domains and human constant domains. Their intrinsic activities were analyzed based on a functional assay monitoring inhibition of ligand (HGF)-dependent c-Met receptor phosphorylation.

Upon PCR-cloning of mouse variable domain sequences (VH, VL), chimeric Mabs were constructed upon ligation of a {Nhe1-Bcl1} restriction fragment carrying either mouse VH or VL sequences into a pCEP4 vector (InVitrogen, US) carrying the entire coding sequence of the constant domain of either a human light chain Ckappa or a human heavy chain [CH1-Hinge-CH2-CH3] of an IgG1 immunoglobulin. All cloning steps were performed according to conventional molecular biology techniques as described in the Laboratory manual (Sambrook and Russel, 2001) or according to the supplier's instructions. Each genetic construct was fully validated by nucleotide sequencing using Big Dye terminator cycle sequencing kit (Applied Biosystems, US) and analyzed using a 3100 Genetic Analyzer (Applied Bio systems, US). Production of the corresponding chimeric Mabs was performed using suspension-adapted HEK293 EBNA cells (InVitrogen, US) grown in serum-free medium Excell 293 (SAFC Biosciences) supplemented with 6 mM glutamine. Transient transfection was performed using linear 25 kDa polyethyleneimine (PEI) (Polysciences). Cultivation process was monitored on the basis of cell viability and Mab production. Mabs were purified using a conventional chromatography approach on a Protein A resin (GE Healthcare, US).

All different forms of Mabs were produced at levels suitable with functional evaluations. Productivity levels are typically ranging between 15 and 30 mg/l of purified Mabs.

Functional evaluations were performed on A549 human lung cancer cells. c-Met receptor phosphorylation status was monitored on cell lysates using a specific capture ELISA assay. A goat anti-c-Met Mab (R&D, ref AF276) was used as capture antibody whereas the detection antibody corresponded to an anti-phospho-c-Met Mab (Biosource ref KHO0281). Luminescence readings were recorded on a Mithras LB920 multimode plate reader (Berthold).

All three murine Mabs 11E1, 224G11 and 227H1 yielded comparable intrinsic activities on c-Met receptor phosphorylation: almost no agonist activity by their own (less than 5% of HGF effect, FIG. 1A), and a strong inhibition of HGF [100 ng/ml]-induced c-Met receptor phosphorylation (>70% inhibition of HGF effect, FIG. 1B). Very surprisingly, by modifying exclusively the Mab's constant domain to switch from a mouse IgG1/kappa to a human IgG1 kappa, a complete modification of the intrinsic activities of the resulting chimeric Mabs was observed (FIGS. 1A-1B). Indeed, strong agonism (reaching 20% of HGF effect for c11E1, FIG. 1A) was observed associated with an important decrease in the antagonist efficacy (only remaining 60% of inhibition of HGF effect for c224G11, FIG. 1B). This effect was independent of the variable domain of the antibody since the same phenomenon was observed for the three investigated Mabs (the 11E1, 224G11 and 227H1 monoclonal antibodies are secreted by the hybridoma deposited at the Collection Nationale de Cultures de Microorganismes (CNCM, National Collection of Microorganism Cultures) (Institut Pasteur, Paris, France) on Mar. 14, 2007 under the numbers CNCM 1-3724 (corresponding to 11E1), I-3731 (corresponding to 224G11) and 1-3732 (corresponding to 227H1) (see the PCT patent application published under the number WO 2009/007427).

EXAMPLE 2

Design, Cloning and Production of Engineered Hinge Versions

Based on the observation made above, it is hypothesized that the impaired pharmacological profile observed upon reformatting of mouse IgG1 into human IgG1 Mabs was due to the human IgG1 domain.

On one hand, it was known in the literature that activation of the c-Met receptor was associated with its dimerization, and that inhibition of c-Met receptor dimerization may inhibit c-Met receptor phosphorylation and downstream signaling.

On the other hand, Mabs are by essence divalent molecules due to their inherent structural basis and thus, they may act as inducers of c-Met receptor dimerization.

Therefore, it is hypothesized that by restricting the conformational flexibility of chimeric Mabs, such as rotation, bending or wagging (see Roux et al., 1997), it could be possible to regain the intrinsic activities of interest (strong antagonism and weak agonism) of the parental murine Mabs. This hypothesis is reinforced by analysis of the respective sequences of mouse and human IgG1 hinge regions (also referred as IgG1 H-region):

```
Mouse IgG1 H-region PRDCGCKPCICT    (SEQ ID No. 1)

Human IgG1 H-region PKSCDKTHTCPPCP  (SEQ ID No. 11)

Human IgG2 H-region RKCCVECPPCP     (SEQ ID No. 7)
```

This alignment shows that the mouse IgG1 H-region is shorter and contains one additional disulfide bridge (Cys) as compared to the human IgG1 H-region. It also shows that the human IgG2 H-region resembles that of mouse IgG1 H-region, both in its length (11 AA) and number of disulfide bridges (4).

Therefore, it is speculated that increased rigidity of the human IgG1 H-region could be obtained by introducing stabilizing mutations such as Cys residues and/or by shortening of this particular segment. This putative increased rigidity of the H-region may be associated with improved functional properties of the engineered human IgG1 Mab.

A first series of 7 engineered versions have been designed (Table 2) by making chimeric H-regions upon exchange of either N-terminal or C-terminal hinge portions between mouse and human sequences. Construction of an IgG2 equivalent was as well performed.

TABLE 2

| WT-IgG2 | WT-IgG$_1$ | | | Variants | | | | |
|---|---|---|---|---|---|---|---|---|
| Hu-IgG$_2$ | Hu-IgG$_1$ | Mu-IgG$_1$ | MH-IgG$_1$ | MMCH-IgG$_1$ | MMH-IgG$_1$ | MUP9H-IgG$_1$ | MUC7H-IgG$_1$ | TH7CΔ6,9-IgG$_1$ |
| — | P | P | P | P | P | P | P | P |
| R | K | R | R | K | K | R | R | K |
| K | S | D | D | S | S | D | D | S |
| C | C | C | C | C | C | C | C | C |
| — | D | G | G | G | G | G | G | D |
| — | K | — | — | — | — | — | — | — |
| C | T | C | C | C | C | C | C | C |
| V | H | K | K | K | K | K | H | H |
| E | T | P | P | P | P | P | T | — |
| C | C | C | C | C | C | C | C | C |
| P | P | I | I | I | I | P | P | P |
| P | P | — | — | — | — | P | P | P |
| C | C | C | C | C | C | C | C | C |
| P | P | T | T | T | P | P | P | P |

An additional series of 28 mutants in the H-region were designed and constructed in order to evaluate the influence of either introduction of one additional cysteine residue within the H-region, or making a deletion of at least one amino acid, or combining simultaneously addition of one cysteine and deletion of et least one amino acid within the H-region.

This novel series of hinge mutants is described in Table 3.

TABLE 3

| | #01 | #02 | #03 | #04 | #05 | #06 | #07 | #08 | #09 | #10 | #11 | #12 | #13 | #14 |
|---|---|---|---|---|---|---|---|---|---|---|---|---|---|---|
| C1 | C | K | S | C | D | K | T | H | T | C | P | P | C | P |
| C2 | P | C | S | C | D | K | T | H | T | C | P | P | C | P |
| C3 | P | K | C | C | D | K | T | H | T | C | P | P | C | P |
| C5 | P | K | S | C | C | K | T | H | T | C | P | P | C | P |
| C6 | P | K | S | C | D | C | T | H | T | C | P | P | C | P |
| C7 | P | K | S | C | D | K | C | H | T | C | P | P | C | P |
| C8 | P | K | S | C | D | K | T | C | T | C | P | P | C | P |
| C9 | P | K | S | C | D | K | T | H | C | C | P | P | C | P |
| C11 | P | K | S | C | D | K | T | H | T | C | C | P | C | P |
| C12 | P | K | S | C | D | K | T | H | T | C | P | C | C | P |
| C14 | P | K | S | C | D | K | T | H | T | C | P | P | C | C |
| Δ2 | P | — | S | C | D | K | T | H | T | C | P | P | C | P |
| Δ6 | P | K | S | C | D | — | T | H | T | C | P | P | C | P |
| Δ9 | P | K | S | C | D | K | T | H | — | C | P | P | C | P |
| Δ1-3 | — | K | — | C | D | K | T | H | T | C | P | P | C | P |
| Δ2-5 | P | — | S | C | — | K | T | H | T | C | P | P | C | P |
| Δ6-9 | P | K | S | C | D | — | T | H | — | C | P | P | C | P |
| Δ5-6 | P | K | S | C | — | — | T | H | T | C | P | P | C | P |
| Δ8-11 | P | K | S | C | D | K | T | — | T | C | — | P | C | P |
| Δ9-14 | P | K | S | C | D | K | T | H | — | C | P | P | C | — |
| C7Δ6 | P | K | S | C | D | — | C | H | T | C | P | P | C | P |
| C6Δ9 | P | K | S | C | D | C | T | H | — | C | P | P | C | P |
| C2Δ5-7 | P | C | S | C | — | K | — | H | T | C | P | P | C | P |

TABLE 3-continued

|           | #01 | #02 | #03 | #04 | #05 | #06 | #07 | #08 | #09 | #10 | #11 | #12 | #13 | #14 |
|-----------|-----|-----|-----|-----|-----|-----|-----|-----|-----|-----|-----|-----|-----|-----|
| C5Δ2-6    | P   | —   | S   | C   | C   | —   | T   | H   | T   | C   | P   | P   | C   | P   |
| C9Δ2-7    | P   | —   | S   | C   | D   | K   | —   | H   | C   | C   | P   | P   | C   | P   |
| Δ4-5-6    | P   | K   | S   | —   | —   | —   | T   | H   | T   | C   | P   | P   | C   | P   |
| Δ5-6-7-8  | P   | K   | S   | C   | —   | —   | —   | —   | T   | C   | P   | P   | C   | P   |
| IgG1/IgG2 | P   | K   | S   | C   | D   | K   | C   | V   | E   | C   | P   | P   | C   | P   |

As an example of hinge engineering, the variable domain (heavy and light chains) of a mouse anti-c-Met Mab—called 224G11, was chosen.

These mouse sequences were fused in a first instance to human constant domains [Ckappa] for the light chain and [CH1-Hinge-CH2-CH3] for the human IgG1 heavy chain. Modification of the hinge region was performed by exchanging a {Nhe1-Bel1} restriction fragment by the equivalent portion carrying the desired modifications, each respective {Nhe1-Bcl1} fragment being synthesized by global gene synthesis (Genecust, LU). All new hinge mutants were constructed on the same basis.

All cloning steps were performed according to conventional molecular biology techniques as described in the Laboratory manual (Sambrook and Russel, 2001) or according to the supplier's instructions. Each genetic construct was fully validated by nucleotide sequencing using Big Dye terminator cycle sequencing kit (Applied Biosystems, US) and analyzed using a 3100 Genetic Analyzer (Applied Biosystems, US).

Suspension-adapted HEK293 EBNA cells (InVitrogen, US) were routinely grown in 250 ml flasks in 50 ml of serum-free medium Excell 293 (SAFC Biosciences) supplemented with 6 mM glutamine on an orbital shaker (110 rpm rotation speed). Transient transfection was performed with $2.10^6$ cells/ml using linear 25 kDa polyethyleneimine (PEI) (Polysciences) prepared in water at a final concentration of 1 mg/ml mixed and plasmid DNA (final concentration of 1.25 µg/ml for heavy to light chain plasmid ratio of 1:1). At 4 hours post-transfection, the culture was diluted with one volume of fresh culture medium to achieve a final cell density of $10^6$ cells/ml. Cultivation process was monitored on the basis of cell viability and Mab production. Typically, cultures were maintained for 4 to 5 days. Mabs were purified using a conventional chromatography approach on a Protein A resin (GE Healthcare, US).

All different forms of Mabs were produced at levels suitable with functional evaluations. Productivity levels are typically ranging between 15 and 30 mg/l of purified Mabs.

EXAMPLE 3

Evaluation of the Engineered Mabs in a Phospho-c-Met-Specific ELISA Assay

A549 cells were seeded in a 12 multiwell (MW) plate in complete growth medium [F12K+10% FCS]. Cells were starved for 16 hours before stimulation with HGF [100 ng/ml], and each Mab to be tested was added at its final concentration of 30 µg/ml 15 minutes prior to ligand stimulation. Ice-cold lysis buffer was added 15 minutes after the addition of HGF to stop the phosphorylation reaction. Cells were scaped mechanically and cell lysates were collected by centrifugation at 13000 rpm for 10 min. at 4° C. and correspond to the supernatant phase. Protein content was quantified using a BCA kit (Pierce) and stored at −20° C. until use. The phosphorylation status of c-Met was quantified by ELISA. A goat anti-c-Met Mab (R&D, ref AF276) was used as a capture antibody (overnight coating at 4° C.) and after a saturation step with a TBS-BSA 5% buffer (1 hour at room temperature (RT)), 25 µg of protein lysates were added to each well of the coated 96MW plate. After a 90 minutes incubation at RT, plates were washed four time and the detection antibody was added (anti-phospho-c-Met Mab, directed against the phosphorylated Tyr residues at position 1230, 1234 and 1235). After an additional 1 hour incubation and 4 washes, an anti-rabbit antibody coupled to HRP (Biosource) was added for 1 hour at RT, and the luminescence detection was performed by adding Luminol. Luminescence readings were on a Mithras LB920 multi-mode plate reader (Berthold).

A series of engineered versions of the heavy chain hinge domain was constructed and assayed in the c-Met receptor phosphorylation assay. As shown in FIG. 2A, compared to 224G11[IgG1-Chim], an important reduction of the agonist effect associated with the hIgG1/kappa isotype was observed for both the IgG2-based construct and for some engineered IgG1/kappa constructs [MH, MUP9H and TH7, FIG. 2A]. Weakest and comparable agonism activities were obtained with 224G11 [MH-IgG1], containing a fully murine IgG1 hinge region and 224G11 [TH7], containing the most human engineered IgG1 hinge region. A concomitant increase in antagonist efficacy was as well obtained [FIG. 2B]. Thus, both IgG2-based and engineered hIgG1/kappa-based TH7 hinge mutant associated with murine 224G11 variable domain, yielded functional activities almost similar to that of the mouse 224G11 Mab. However, the comparison of agonistic/antagonistic activities of 224G11[MMCH-IgG1-chim] with 224G11[IgG1-chim] demonstrated that an increased antagonistic activity could be obtain by antibody engineering irrespectively of the intrinsic agonistic properties of such antibody.

A second series of engineered versions of the heavy chain hinge domain was constructed and assayed in the c-Met receptor phosphorylation assay. As shown in FIG. 11A, amino-acid substitution in heavy chain hinge domain introducing cystein residues modified agonist effect of antibodies. Indeed, in one hand, some mutated versions exhibited weaker agonist effect than c224G11, as for example c224G11[C2], c224G11[C3], c224G11[C5], c224G11[C6] or c224G11[C7] while others increased agonist effect as c224G11[C11], c224G11[C12] and c224G11[C14]. Moreover, amino-acid deletions in the heavy chain hinge domain associated or not with amino-acid substations also modified agonist properties of the antibodies [FIG. 11B]. For example, c224G11[Δ1-3], c224G11[Δ4-5-6], c224G11[Δ5-6-7-8], c224G11[C7Δ6], c224G11[C6Δ9], c224G11[C2Δ5-7], c224G11[C5Δ2-6] or c224G11[C9Δ2-7] showed a weaker agonist effect than c224G11 while c224G11 [Δ8-11] exhibited a stronger agonist effect. As c224G11[TH7], all the new versions exhibiting a weaker agonist effect showed a concomitant increase in antagonist efficacy [FIGS. 12A and 12B] while those exhibiting a stronger agonist effect had a weaker antagonist efficacy.

In the present application, the use of square brackets is not necessary and, as en example, the reference [224G11] [IgG2chim] must be considered as identical to 224G11IgG2chim. In a same way, to indicate that the antibody is a murine one, the expression murine or the letter m can be added; to indicate that the antibody is a chimeric one, the expression chim or the letter c can be added and; to indicate that the antibody is a humanized one, the expression hum or the letter h can be added. As an example, the chimeric antibody 224G1IgG2 can be referred as c224G11IgG2, c224G11[IgG2], c[224G11]IgG2, c[224G11] [IgG2], 224G11IgG2chim, 224G11 [IgG2chim], [224G11]IgG2chim or [224G11] [IgG2chim].

The symbol Δ means deletion.

EXAMPLE 4

BRET Analysis

In a first set of experiments, it was controlled that irrelevant mouse IgG1, human IgG1 and human IgG2 had no effect of HGF induced BRET signal in both BRET models (FIG. 3). Those Mabs were used further as controls.

The effect of IgG1 chimeric forms of mouse 224G11 Mab ([224G11] chim), mouse 11E1 Mab ([11E1] chim) and mouse 227H1 Mab ([227H1] chim) on c-Met dimerization and c-met activation BRET model were then evaluated.

Figure 5:
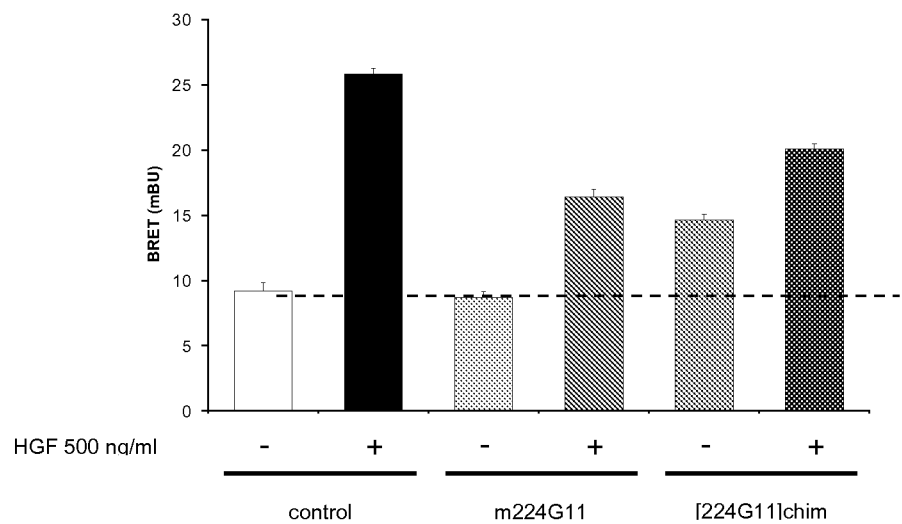

While mouse 224G11 Mab inhibited 59% of the HGF induced BRET signal on c-Met dimerization model, [224G11] chim Mab inhibited only 29% (FIG. 4). [224G11] chim antibody was also less effective in inhibiting HGF induced c-Met activation since [224G11] chim and m224G11 antibodies inhibited 34.5% and 56.4% of HGF induced BRET signal (FIG. 5). Moreover, m224G11 alone had no effect on c-Met activation while [224G11] chim had a partial agonist effect on c-Met activation corresponding to 32.9% of the HGF induced signal. This partial agonist effect of the [224G11] chim was also seen on c-Met dimerization BRET model since [224G11] chim alone induced a BRET increase corresponding to 46.6% of HGF-induced signal versus 21.3% for m224G11.

The agonist efficacy of the second series of engineered versions of the heavy chain hinge domain was evaluated in c-Met activation BRET model (FIGS. 13A and 13B). In contrast to c224G11, which had a partial agonist effect on c-Met activation, different hinge mutated chimeric forms of 224G11 antibody comprising amino-acid substitution, amino-acid deletion or both showed no significant effect on c-Met activation alone for c224G11[C2], c224G11[C3], c224G11[C5], c224G11[C6], c224G11[C7], c224G11[Δ1-3], c224G11[Δ4-5-6], c224G11[Δ5-6-7-8], c224G11[C7Δ6], c224G11[C6Δ9], c224G11[C2Δ5-7], c224G11[C5Δ2-6] or c224G11[C9Δ2-7] respectively). In contrast, other hinge mutated chimeric forms showed increased agonist effect as c224G11[Δ6], c224G11[C11], c224G11[C12] and c224G11 [C14].

EXAMPLE 5 c-Met Recognition by Chimeric and Humanized 224G11 Forms

A direct ELISA has been set up to determine the binding ability of the various chimeric and humanized forms on the recombinant c-Met. Briefly recombinant dimeric c-Met from R&D Systems was coated at 1.25 μg/ml on 96-well Immunlon II plates. After an overnight incubation at 4° C., wells were saturated with a 0.5% gelatine/PBS solution. Plates were then incubated for 1 hour at 37° C. before addition of 2 fold dilutions of antibodies to be tested. Plates were incubated an additional hour before addition of a goat anti-mouse IgG HRP for detecting the murine antibody and a goat anti-human Kappa light chain HRP for chimeric and humanized antibody recognition. Plates were incubated for one hour and the peroxydase substrate TMB Uptima was added for 5 mn before neutralization with $H_2SO_4$ 1M. Results presented in FIGS. 6A and 6B showed that all tested forms were comparable for c-Met recognition.

EXAMPLE 6

Effect of Murine and Chimeric Antibodies on HGF-Induced Proliferation of NCI-H441 Cells In Vitro NCI-H441 cells from ATCC were routinely cultured in RPMI 1640 medium (Invitrogen Corporation, Scotland, UK), 10% FCS (Invitrogen Corporation), 1% L-Glutamine (Invitrogen Corporation). For proliferation assays, cells were split 3 days before use so that they were in the confluent phase of growth before plating. NCI-H441 cells were plated in 96-well tissue culture plates at a density of $3.75 \times 10^4$ cells/well in 200 μl of serum free medium (RPMI 1640 medium plus 1% L-Glutamine). Twenty four hours after plating, antibodies to be tested were added to NCI-H441 and incubated at 37° C. for thirty minutes before adding HGF at a final concentration of 400 ng/ml (5 nM) for 142 additional hours. The dose range tested for each antibody is from 10 to 0.0097 μg/ml (final concentration in each well). In this experiment, a murine IgG1 Mab was added as a murine isotype control and the tested antibodies were the following one: m224G11, m11E1, m227H1 and their human IgG1 chimeric forms respectively identified as [224G11] chim, [11E1] chim and [227H1] chim. Wells plated with cells alone−/+HGF were also included. Then cells were pulsed with 0.25 μCi of [$^3$H]Thymidine (Amersham Biosciences AB, Uppsala, Sweden) for 7 hours and 30 minutes. The magnitude of [$^3$H]Thymidine incorporated in trichloroacetic acid-insoluble DNA was quantified by liquid scintillation counting. Results are expressed as non transformed cpm data to better evaluate the potential intrinsic agonist activity that could occur with anti-c-Met Mabs when added alone to tumour cell.

Results described in FIGS. 7A, 7B and 7C demonstrated that, as expected, the murine antibodies displayed no agonist effect when added alone to cancer cells whatever the tested dose. No significant inhibition of the HGF-induced proliferation was observed with the isotype control regarding to the high cpm variations observed for this isotype control in this experiment. When added alone, neither murine m224G11 nor m11E1 or m227H1 showed any agonist effect compared to the mIgG1 isotype control Mab or cells alone. Dose dependent anti-proliferative activities reaching 78%, 80% or 80% were respectively for m224G11, m11E1 or m227H1 Mabs (% inhibition calculation: 100−[(cpm cells+ Mab to be tested−mean cpm background mIgG1)×100/ (mean cpm cells+HGF−mean cpm cells alone)]). Surprisingly, the chimeric form of these 3 Mabs induced a significant, dose dependent agonist effect when added alone with growth stimulations close to the one observed with HGF for [11E1] chim and [227H1] chim respectively. For these 2 antibodies displaying particularly high intrinsic agonist activities, the antagonist effect was significantly decreased with 53 and 21% inhibitory effects compared to 80% observed for their both murine forms. The agonist effect observed with the chimeric [224G11] chim was also dose dependent but it was lower than the ones observed for [11E1] chim and [227H1] chim. However this agonist effect had an impact on the in vitro inhibition of HGF-induced proliferation that shifted from 78% for the murine m224G11 to 50% for its chimeric form. To determine whether such "lower" in vitro intrinsic agonist activity was compatible with an unchanged in vivo effect, both m224G11 and [224G11] chim were produced for in vivo testing. As, in previous studies, the 30 µg/mice dose had demonstrated a significant in vivo activity, that dose was selected for in vivo evaluation.

EXAMPLE 7

In Vivo Comparison of Murine and Chimeric 224G11 Mabs on the NCI-H441 Xenograft Model NCI-H441 is derived from papillary lung adenocarcinoma, expresses high levels of c-Met, and demonstrates constitutive phosphorylation of c-Met RTK.

To evaluate the in vivo effect of antibodies on the NCI-H441 xenograft model, six to eight weeks old athymic mice were housed in sterilized filter-topped cages, maintained in sterile conditions and manipulated according to French and European guidelines. Mice were injected subcutaneously with $9\times10^6$ cells. Then, six days after cell implantation, tumors were measurable (approximately 100 mm³), animals were divided into groups of 6 mice with comparable tumor size and treated first with a loading dose of 60 µg of antibody/mice and then twice a week with 1 mg/dose of each antibody to be tested. The mice were followed for the observation of xenograft growth rate. Tumor volume was calculated by the formula: π(Pi)/6×length×width×height. Results described in FIG. 8 demonstrate that the murine Mab devoided of agonist activity in vivo behave, as expected, as potent antagonist even at the low tested dose. In contrast to what observed with the murine Mab, the chimeric one displayed a very transient in vivo activity and tumor completely escaped to the treatment at D20 post cell injection. This experiment demonstrates clearly that the increase of in vitro agonist effect that resulted in a decrease of antagonist activity was also responsible for a significant in vivo loss of antagonist activity.

EXAMPLE 8

Effect of the Murine 224G11 Mab and of Various Chimeric and Humanized Versions of this Antibody on HGF-Induced Proliferation of NCI-H441 Cells In Vitro NCI-H441 cells from ATCC were routinely cultured in RPMI 1640 medium (Invitrogen Corporation, Scotland, UK), 10% FCS (Invitrogen Corporation), 1% L-Glutamine (Invitrogen Corporation). For proliferation assays, cells were split 3 days before use so that they were in the confluent phase of growth before plating. NCI-H441 cells were plated in 96-well tissue culture plates at a density of $3.75\times10^4$ cells/well in 200 µl of serum free medium (RPMI 1640 medium plus 1% L-Glutamine). Twenty four hours after plating, antibodies to be tested were added to NCI-H441 and incubated at 37° C. for thirty minutes before adding HGF at a final concentration of 400 ng/ml (5 nM) for 142 additional hours. The dose range tested for each antibody is from 10 to 0.0097 µg/ml (final concentration in each well). In this experiment, murine IgG1 Mab was added as a murine isotype control and as an agonist negative control. The tested antibodies were the following one: i) m224G11, ii) its human IgG1 chimeric forms respectively identified as [224G11] chim, [224G11] [MH chim], [224G11] [MUP9H chim], [224G11] [MMCH chim], [224G11] [TH7 chim] iii) its humanized IgG1 forms respectively described as [224G11] [Hz1], [224G11] [Hz2], [224G11] [Hz3]. Wells plated with cells alone–/+HGF were also included. The 5D5 whole antibody from Genentech commercially available at the ATCC as an hybridoma cell line was introduced as a full agonist positive control and thereafter called m5D5. Then cells were pulsed with 0.25 µCi of [³H]Thymidine (Amersham Biosciences AB, Uppsala, Sweden) for 7 hours and 30 minutes. The magnitude of [³H]Thymidine incorporated in trichloroacetic acid-insoluble DNA was quantified by liquid scintillation counting. Results are expressed as non transformed cpm data to better evaluate the potential intrinsic agonist activity that could occur with anti-c-Met Mabs when added alone to tumour cell.

Results described in FIG. 9A demonstrated that as expected neither the isotype control nor the m224G11 displayed any agonist activity on NCI-H441 proliferation. The isotype control was without effect on HGF-induced cell proliferation whereas m224G11 showed a 66% inhibition when added at the final concentration of 10 µg/ml. The m5D5 used as an agonist control showed, as expected, a full dose dependent agonist effect when added alone to the cells. As already observed, the [224G11] chim Mab displayed a significant dose-dependent agonist effect and, a decreased inhibitory activity of this chimeric form was observed: 19% instead of 66% for the murine form. When added alone, the 3 IgG1 humanized Mabs demonstrated dose dependent agonist effects compared to the m224G11 form. [224G11] [Hz1], [224G11] [Hz2] and [224G11] [Hz3] had comparable antagonist activities about 46, 30 and 35%. These activities are significantly lower than the one observed for m224G11. In FIG. 9B, various IgG1 chimeric forms were tested. Compared to [224G11] chim form which displayed a dose-dependent agonist effect when added alone to NCI-H441 cells, the [224G11] [MH chim], [224G11] [MUP9H chim], [224G11] [MMCH chim], [224G11] [TH7 chim] forms were without significant intrinsic agonist effect. Their antagonist activity was higher than the one observed for the m224G11 Mab (57%) with inhibitions reaching 79, 78, 84 and 93% respectively for [224G11] [MH chim], [224G11] [MUP9H chim], [224G11] [MMCH chim] and [224G11] [TH7 chim].

EXAMPLE 9

In Vitro Effect of Various IgG1 Chimeric and Humanized Form of the 224G11 Mab

NCI-H441 cells from ATCC were routinely cultured in RPMI 1640 medium (Invitrogen Corporation, Scotland, UK), 10% FCS (Invitrogen Corporation), 1% L-Glutamine (Invitrogen Corporation). For proliferation assays, cells were split 3 days before use so that they were in the confluent phase of growth before plating. NCI-H441 cells were plated in 96-well tissue culture plates at a density of 3.75×10$^4$ cells/well in 200 µl of serum free medium (RPMI 1640 medium plus 1% L-Glutamine). Twenty four hours after plating, antibodies to be tested were added to NCI-H441 and incubated at 37° C. for thirty minutes before adding HGF at a final concentration of 400 ng/ml (5 nM) for 142 additional hours. The dose range tested for each antibody is from 10 to 0.0097 µg/ml (final concentration in each well). In this experiment, murine IgG1 Mab was added as a background negative control for agonist activity and the tested antibodies were the following one: i) m224G11, ii) its human IgG1 chimeric forms respectively identified as [224G11] chim, [224G11] [TH7 chim] iii) its humanized IgG1 forms respectively described as [224G11] [TH7 Hz1], [224G11] [TH7 Hz3]. Wells plated with cells alone–/+HGF were also included. The 5D5 whole antibody from Genentech commercially available at the ATCC as an hybridoma cell line was introduced as a full agonist positive control and thereafter called m5D5. Then cells were pulsed with 0.25 µCi of [$^3$H]Thymidine (Amersham Biosciences AB, Uppsala, Sweden) for 7 hours and 30 minutes. The magnitude of [$^3$H]Thymidine incorporated in trichloroacetic acid-insoluble DNA was quantified by liquid scintillation counting. Results are expressed as non transformed cpm data to better evaluate the potential intrinsic agonist activity that could occur with anti-c-Met Mabs when added alone to tumour cell.

FIG. 10 showed that the m224G11 Mab displayed the usual inhibitory effect (74% inhibition). The chimeric IgG1 form [224G11] chim had as expected a dose dependant intrinsic agonist effect and a lower antagonist effect compared to the murine form: 33% versus 74% inhibition. The [224G11] [TH7 chim] had a very weak agonist activity in this experiment. In addition, it displayed a high inhibitory effect (81%) close to the one noticed for the murine Mab. The 2 humanized forms had no intrinsic agonist effect and had an antagonist activity close to the ones observed for the murine Mab or the [224G11] [TH7 chim] with respectively 67 and 76% inhibition for [224G11] [TH7 Hz1] and [224G11] [TH7 Hz3].

EXAMPLE 10

Isotype Switching for the Engineered [TH7] Hinge Region

In order to evaluate the modulation of pharmacological properties induced by the [TH7] hinge sequence, corresponding to PKSCDCHCPPCP, into immunoglobulin isotype backbones other than the human IgG1, we genetically transferred the above described [TH7] sequence into human IgG2 and IgG4 backbones. Modification of the hinge region was performed by exchanging a {Nhe1-Bcl1} restriction fragment by the equivalent portion carrying the [TH7] modification, the {Nhe1-Bcl1} fragment being synthesized by global gene synthesis (Genecust, LU). Cloning steps were performed according to conventional molecular biology techniques as described in the Laboratory manual (Sambrook and Russel, 2001) or according to the supplier's instructions. Each genetic construct was fully validated by nucleotide sequencing using Big Dye terminator cycle sequencing kit (Applied Biosystems, US) and analyzed using a 3100 Genetic Analyzer (Applied Biosystems, US). The resulting sequences are described as SEQ ID Nos. 78, 79, 80 and 81 for respectively amino acid and nucleotide sequences of TH7-engineered human IgG2 and IgG4 isotypes (heavy chain only, light chain was identical to the c224G11/human Ckappa used for all other IgG1-based constructs). These novel constructs were applied to the chimeric 224G11 anti-c-Met Mab as described above in example 2.

The corresponding engineered antibodies, c224G11 [IgG2TH7] and c224G11[IgG4TH7], were produced as described above by transient expression in suspension-adapted HEK293 EBNA cells.

EXAMPLE 11

Evaluation of the Engineered Mabs c224G11[IgG2TH7] and c224G11[IgG4TH7] in a Phospho-c-Met-Specific ELISA Assay and BRET Assay TH7 hinge was also introduced on IgG2 and IgG4 chimeric 224G11 Mabs and tested in the c-Met receptor phosphorylation assay. As shown in 14A and 14B, c224G11 [IgG2TH7] and c224G11[IgG4TH7] induced a faint agonist effect alone but significantly weaker than c224G11 Mab, and exhibited an antagonist effect comparable to the murine form of 224G11 Mab (m224G11). This result was confirmed on c-Met activation BRET model (FIG. 15), where c224G11 [IgG2TH7] and c224G11[IgG4TH7] showed also a weaker agonist than c224G11 Mab.

Thus, TH7 hinge mutation introduced on IgG2 or IgG4 Mab format gave functional antibodies with similar properties than c224G11[TH7].

EXAMPLE 12

Cell Adhesion Assay

PC3 prostate cancer cells were detached from dishes with trypsin, washed 3 times with serum-free F12k medium and resuspended in the same medium. Cells (100,000 cells/well) were plated on 96-well plates coated with Laminin 1 at 1 µg/ml. The following forms of the anti-CD151 Mab to be tested were added simultaneously at the final concentration of 10 µg/ml: the murine IgG1 Mab m214B2, the non modified chimeric IgG1 antibody form called c214B2 and the chimeric IgG1 antibody form with the TH7 modification called cTH7-214B2.

CD151 is a membrane protein belonging to the tetraspanin family and the anti-CD151 Mab 214B2, produced by the hybridoma 1-3919 filed at the CNCM on 21 Feb. 2008, is described in the published patent application WO 2009/136070.

Murine and human IgG1 antibodies were used as isotype control antibodies. The final conditions were as follows: 100000 cells/well and antibodies at 10 µg/ml. After one hour incubation at 37° C., the plates were flicked off and washed twice with serum-free F12k medium. Before the analysis 100 µl of serum-free F12k medium were distributed in each well. To assess the effect of antibodies on cell adhesion wells, were photographed under a phase-contrast microscope (FIG. 16). Then the number of adhered cells was determined using an ATP assay (FIG. 17).

The murine 214B2 and chimeric TH7-214B2 antibodies were able to modify cell-to-cell interactions (FIG. 16) and to increase equivalently PC3 cell adhesion (FIG. 17), whereas no effect was observed with the non modified chimeric form of 214B2 (c214B2) which was comparable to the human IgG1 isotype control antibody.

The invention claimed is:

1. A process of improving a monoclonal antibody's ability to inhibit the binding of a transmembrane receptor to its ligand, wherein said antibody comprises a hinge region, or of a divalent functional fragment of said antibody comprising a hinge region, wherein said process comprises:

modifying an antibody that is capable of inhibiting the binding of a transmembrane receptor to its ligand by deleting, adding, or substituting at least one amino acid in the amino acid sequence of said hinge region of said antibody;

selecting the modified antibody wherein the modification improves the antibody's ability to inhibit the binding of the transmembrane receptor to its ligand over a modified antibody wherein the modification does not improve the antibody's ability to inhibit the binding of the transmembrane receptor to its ligand;

wherein the hinge that comprises a modification that improves the antibody's ability to inhibit the binding of the transmembrane receptor to its ligand;

comprises SEQ ID No. 6.

2. The process according to claim 1, wherein said monoclonal antibody is a divalent antibody.

3. The process according to claim 1, wherein said monoclonal antibody is a chimeric antibody.

4. The process according to claim 1, wherein said monoclonal antibody is a humanized antibody.

5. The process according to claim 1, wherein said monoclonal antibody is a human antibody.

6. The process according to claim 1, wherein said monoclonal antibody is an IgG1 antibody.

7. The process of claim 1, wherein said transmembrane receptor is selected from tyrosine kinase receptors, tetraspanin, and G-protein coupled receptors (GPCRs).

* * * * *

SEQUENCE LISTING

<160> NUMBER OF SEQ ID NOS: 81

<210> SEQ ID NO 1
<211> LENGTH: 12
<212> TYPE: PRT
<213> ORGANISM: artificial
<220> FEATURE:
<223> OTHER INFORMATION: artificial modified hinge region

<400> SEQUENCE: 1

Pro Arg Asp Cys Gly Cys Lys Pro Cys Ile Cys Thr
1               5                   10

<210> SEQ ID NO 2
<211> LENGTH: 12
<212> TYPE: PRT
<213> ORGANISM: artificial
<220> FEATURE:
<223> OTHER INFORMATION: artificial modified hinge region

<400> SEQUENCE: 2

Pro Lys Ser Cys Gly Cys Lys Pro Cys Ile Cys Thr
1               5                   10

<210> SEQ ID NO 3
<211> LENGTH: 12
<212> TYPE: PRT
<213> ORGANISM: artificial
<220> FEATURE:
<223> OTHER INFORMATION: artificial modified hinge region

<400> SEQUENCE: 3

Pro Lys Ser Cys Gly Cys Lys Pro Cys Ile Cys Pro
1               5                   10

<210> SEQ ID NO 4
<211> LENGTH: 13
<212> TYPE: PRT
<213> ORGANISM: artificial
<220> FEATURE:
<223> OTHER INFORMATION: artificial modified hinge region

<400> SEQUENCE: 4

Pro Arg Asp Cys Gly Cys Lys Pro Cys Pro Pro Cys Pro
1               5                   10

<210> SEQ ID NO 5
<211> LENGTH: 13
<212> TYPE: PRT
<213> ORGANISM: artificial
<220> FEATURE:
<223> OTHER INFORMATION: artificial modified hinge region

<400> SEQUENCE: 5

Pro Arg Asp Cys Gly Cys His Thr Cys Pro Pro Cys Pro
1               5                   10

<210> SEQ ID NO 6
<211> LENGTH: 12
<212> TYPE: PRT
<213> ORGANISM: artificial
<220> FEATURE:
<223> OTHER INFORMATION: artificial modified hinge region

<400> SEQUENCE: 6

Pro Lys Ser Cys Asp Cys His Cys Pro Pro Cys Pro
1               5                   10

<210> SEQ ID NO 7
<211> LENGTH: 11
<212> TYPE: PRT
<213> ORGANISM: homo sapiens

<400> SEQUENCE: 7

Arg Lys Cys Cys Val Glu Cys Pro Pro Cys Pro
1               5                   10

<210> SEQ ID NO 8
<211> LENGTH: 18
<212> TYPE: PRT
<213> ORGANISM: homo sapiens

<400> SEQUENCE: 8

Pro Ser Thr Pro Pro Thr Pro Ser Pro Ser Thr Pro Pro Thr Pro Ser
1               5                   10                  15

Pro Ser

<210> SEQ ID NO 9
<211> LENGTH: 5
<212> TYPE: PRT
<213> ORGANISM: homo sapiens

<400> SEQUENCE: 9

Pro Pro Pro Pro Pro
1               5

<210> SEQ ID NO 10
<211> LENGTH: 56
<212> TYPE: PRT
<213> ORGANISM: homo sapiens

<400> SEQUENCE: 10

Ser Pro Lys Ala Gln Ala Ser Ser Val Pro Thr Ala Gln Pro Gln Ala
1               5                   10                  15

Glu Gly Ser Leu Ala Lys Ala Thr Thr Ala Pro Ala Thr Thr Arg Asn
                20                  25                  30

Thr Arg Gly Gly Glu Glu Lys Lys Lys Glu Lys Glu Lys Glu Glu Gln
            35                  40                  45

Glu Glu Arg Glu Thr Lys Thr Pro
    50                  55

<210> SEQ ID NO 11
<211> LENGTH: 14
<212> TYPE: PRT
<213> ORGANISM: homo sapiens

<400> SEQUENCE: 11

Pro Lys Ser Cys Asp Lys Thr His Thr Cys Pro Pro Cys Pro
1               5                   10

<210> SEQ ID NO 12
<211> LENGTH: 63
<212> TYPE: PRT
<213> ORGANISM: homo sapiens

<400> SEQUENCE: 12

Leu Lys Thr Pro Leu Phe Thr Gly Asp Thr Thr His Thr Cys Pro Arg
1               5                   10                  15

Cys Pro Glu Pro Lys Ser Cys Asp Thr Pro Pro Pro Cys Pro Arg Cys

```
                    20                  25                  30
Pro Glu Pro Lys Ser Cys Asp Thr Pro Pro Cys Pro Arg Cys Pro
        35                  40                  45

Glu Pro Lys Ser Cys Asp Thr Pro Pro Cys Pro Arg Cys Pro
    50                  55                  60
```

```
<210> SEQ ID NO 13
<211> LENGTH: 11
<212> TYPE: PRT
<213> ORGANISM: homo sapiens

<400> SEQUENCE: 13

Ser Lys Tyr Gly Pro Pro Cys Pro Ser Cys Pro
1               5                   10

<210> SEQ ID NO 14
<211> LENGTH: 12
<212> TYPE: PRT
<213> ORGANISM: mus musculus

<400> SEQUENCE: 14

Pro Arg Asp Cys Gly Cys Lys Pro Cys Ile Cys Thr
1               5                   10

<210> SEQ ID NO 15
<211> LENGTH: 36
<212> TYPE: DNA
<213> ORGANISM: artificial sequence
<220> FEATURE:
<223> OTHER INFORMATION: artificial modified hinge region

<400> SEQUENCE: 15
ccccgggact gtgggtgcaa gccttgcatt tgtacc                           36

<210> SEQ ID NO 16
<211> LENGTH: 36
<212> TYPE: DNA
<213> ORGANISM: artificial sequence
<220> FEATURE:
<223> OTHER INFORMATION: artificial modified hinge region

<400> SEQUENCE: 16
cccaagagct gtgggtgcaa gccttgcatt tgtacc                           36

<210> SEQ ID NO 17
<211> LENGTH: 36
<212> TYPE: DNA
<213> ORGANISM: artificial sequence
<220> FEATURE:
<223> OTHER INFORMATION: artificial modified hinge region

<400> SEQUENCE: 17
ccaaagagct gcggctgcaa gccttgtatc tgtccc                           36

<210> SEQ ID NO 18
<211> LENGTH: 39
<212> TYPE: DNA
<213> ORGANISM: artificial sequence
<220> FEATURE:
<223> OTHER INFORMATION: artificial modified hinge region

<400> SEQUENCE: 18
ccacgggact gtggctgcaa gccctgccct ccgtgtcca                        39
```

<210> SEQ ID NO 19
<211> LENGTH: 39
<212> TYPE: DNA
<213> ORGANISM: artificial sequence
<220> FEATURE:
<223> OTHER INFORMATION: artificial modified hinge region

<400> SEQUENCE: 19
cccagagact gtgggtgtca cacctgccct ccttgtcct                    39

<210> SEQ ID NO 20
<211> LENGTH: 36
<212> TYPE: DNA
<213> ORGANISM: artificial sequence
<220> FEATURE:
<223> OTHER INFORMATION: artificial modified hinge region

<400> SEQUENCE: 20
cccaaaagct gcgattgcca ctgtcctcca tgtcca                       36

<210> SEQ ID NO 21
<211> LENGTH: 33
<212> TYPE: DNA
<213> ORGANISM: homo sapiens

<400> SEQUENCE: 21
aggaagtgct gtgtggagtg ccccccctgc cca                          33

<210> SEQ ID NO 22
<211> LENGTH: 14
<212> TYPE: PRT
<213> ORGANISM: artificial
<220> FEATURE:
<223> OTHER INFORMATION: artificial modified hinge region

<400> SEQUENCE: 22

Cys Lys Ser Cys Asp Lys Thr His Thr Cys Pro Pro Cys Pro
1               5                   10

<210> SEQ ID NO 23
<211> LENGTH: 14
<212> TYPE: PRT
<213> ORGANISM: artificial
<220> FEATURE:
<223> OTHER INFORMATION: artificial modified hinge region

<400> SEQUENCE: 23

Pro Cys Ser Cys Asp Lys Thr His Thr Cys Pro Pro Cys Pro
1               5                   10

<210> SEQ ID NO 24
<211> LENGTH: 14
<212> TYPE: PRT
<213> ORGANISM: artificial
<220> FEATURE:
<223> OTHER INFORMATION: artificial modified hinge region

<400> SEQUENCE: 24

Pro Lys Cys Cys Asp Lys Thr His Thr Cys Pro Pro Cys Pro
1               5                   10

<210> SEQ ID NO 25
<211> LENGTH: 14
<212> TYPE: PRT
<213> ORGANISM: artificial
<220> FEATURE:
<223> OTHER INFORMATION: artificial modified hinge region

```
<400> SEQUENCE: 25

Pro Lys Ser Cys Cys Lys Thr His Thr Cys Pro Pro Cys Pro
1               5                   10

<210> SEQ ID NO 26
<211> LENGTH: 14
<212> TYPE: PRT
<213> ORGANISM: artificial
<220> FEATURE:
<223> OTHER INFORMATION: artificial modified hinge region

<400> SEQUENCE: 26

Pro Lys Ser Cys Asp Cys Thr His Thr Cys Pro Pro Cys Pro
1               5                   10

<210> SEQ ID NO 27
<211> LENGTH: 14
<212> TYPE: PRT
<213> ORGANISM: artificial
<220> FEATURE:
<223> OTHER INFORMATION: artificial modified hinge region

<400> SEQUENCE: 27

Pro Lys Ser Cys Asp Lys Cys His Thr Cys Pro Pro Cys Pro
1               5                   10

<210> SEQ ID NO 28
<211> LENGTH: 14
<212> TYPE: PRT
<213> ORGANISM: artificial
<220> FEATURE:
<223> OTHER INFORMATION: artificial modified hinge region

<400> SEQUENCE: 28

Pro Lys Ser Cys Asp Lys Thr Cys Thr Cys Pro Pro Cys Pro
1               5                   10

<210> SEQ ID NO 29
<211> LENGTH: 14
<212> TYPE: PRT
<213> ORGANISM: artificial
<220> FEATURE:
<223> OTHER INFORMATION: artificial modified hinge region

<400> SEQUENCE: 29

Pro Lys Ser Cys Asp Lys Thr His Cys Cys Pro Pro Cys Pro
1               5                   10

<210> SEQ ID NO 30
<211> LENGTH: 14
<212> TYPE: PRT
<213> ORGANISM: artificial
<220> FEATURE:
<223> OTHER INFORMATION: artificial modified hinge region

<400> SEQUENCE: 30

Pro Lys Ser Cys Asp Lys Thr His Thr Cys Cys Pro Cys Pro
1               5                   10

<210> SEQ ID NO 31
<211> LENGTH: 14
<212> TYPE: PRT
<213> ORGANISM: artificial
<220> FEATURE:
<223> OTHER INFORMATION: artificial modified hinge region
```

```
<400> SEQUENCE: 31

Pro Lys Ser Cys Asp Lys Thr His Thr Cys Pro Cys Cys Pro
1               5                   10

<210> SEQ ID NO 32
<211> LENGTH: 14
<212> TYPE: PRT
<213> ORGANISM: artificial
<220> FEATURE:
<223> OTHER INFORMATION: artificial modified hinge region

<400> SEQUENCE: 32

Pro Lys Ser Cys Asp Lys Thr His Thr Cys Pro Pro Cys Cys
1               5                   10

<210> SEQ ID NO 33
<211> LENGTH: 13
<212> TYPE: PRT
<213> ORGANISM: artificial
<220> FEATURE:
<223> OTHER INFORMATION: artificial modified hinge region

<400> SEQUENCE: 33

Pro Ser Cys Asp Lys Thr His Thr Cys Pro Pro Cys Pro
1               5                   10

<210> SEQ ID NO 34
<211> LENGTH: 13
<212> TYPE: PRT
<213> ORGANISM: artificial
<220> FEATURE:
<223> OTHER INFORMATION: artificial modified hinge region

<400> SEQUENCE: 34

Pro Lys Ser Cys Asp Thr His Thr Cys Pro Pro Cys Pro
1               5                   10

<210> SEQ ID NO 35
<211> LENGTH: 13
<212> TYPE: PRT
<213> ORGANISM: artificial
<220> FEATURE:
<223> OTHER INFORMATION: artificial modified hinge region

<400> SEQUENCE: 35

Pro Lys Ser Cys Asp Lys Thr His Cys Pro Pro Cys Pro
1               5                   10

<210> SEQ ID NO 36
<211> LENGTH: 12
<212> TYPE: PRT
<213> ORGANISM: artificial
<220> FEATURE:
<223> OTHER INFORMATION: artificial modified hinge region

<400> SEQUENCE: 36

Lys Cys Asp Lys Thr His Thr Cys Pro Pro Cys Pro
1               5                   10

<210> SEQ ID NO 37
<211> LENGTH: 12
<212> TYPE: PRT
<213> ORGANISM: artificial
<220> FEATURE:
<223> OTHER INFORMATION: artificial modified hinge region

<400> SEQUENCE: 37
```

```
Pro Ser Cys Lys Thr His Thr Cys Pro Pro Cys Pro
1               5                   10
```

<210> SEQ ID NO 38
<211> LENGTH: 12
<212> TYPE: PRT
<213> ORGANISM: artificial
<220> FEATURE:
<223> OTHER INFORMATION: artificial modified hinge region

<400> SEQUENCE: 38

```
Pro Lys Ser Cys Asp Thr His Cys Pro Pro Cys Pro
1               5                   10
```

<210> SEQ ID NO 39
<211> LENGTH: 12
<212> TYPE: PRT
<213> ORGANISM: artificial
<220> FEATURE:
<223> OTHER INFORMATION: artificial modified hinge region

<400> SEQUENCE: 39

```
Pro Lys Ser Cys Thr His Thr Cys Pro Pro Cys Pro
1               5                   10
```

<210> SEQ ID NO 40
<211> LENGTH: 12
<212> TYPE: PRT
<213> ORGANISM: artificial
<220> FEATURE:
<223> OTHER INFORMATION: artificial modified hinge region

<400> SEQUENCE: 40

```
Pro Lys Ser Cys Asp Lys Thr Thr Cys Pro Cys Pro
1               5                   10
```

<210> SEQ ID NO 41
<211> LENGTH: 12
<212> TYPE: PRT
<213> ORGANISM: artificial
<220> FEATURE:
<223> OTHER INFORMATION: artificial modified hinge region

<400> SEQUENCE: 41

```
Pro Lys Ser Cys Asp Lys Thr His Cys Pro Pro Cys
1               5                   10
```

<210> SEQ ID NO 42
<211> LENGTH: 13
<212> TYPE: PRT
<213> ORGANISM: artificial
<220> FEATURE:
<223> OTHER INFORMATION: artificial modified hinge region

<400> SEQUENCE: 42

```
Pro Lys Ser Cys Asp Cys His Thr Cys Pro Pro Cys Pro
1               5                   10
```

<210> SEQ ID NO 43
<211> LENGTH: 13
<212> TYPE: PRT
<213> ORGANISM: artificial
<220> FEATURE:
<223> OTHER INFORMATION: artificial modified hinge region

<400> SEQUENCE: 43

```
Pro Lys Ser Cys Asp Cys Thr His Cys Pro Pro Cys Pro
1               5                   10
```

<210> SEQ ID NO 44
<211> LENGTH: 12
<212> TYPE: PRT
<213> ORGANISM: artificial
<220> FEATURE:
<223> OTHER INFORMATION: artificial modified hinge region

<400> SEQUENCE: 44

```
Pro Cys Ser Cys Lys His Thr Cys Pro Pro Cys Pro
1               5                   10
```

<210> SEQ ID NO 45
<211> LENGTH: 12
<212> TYPE: PRT
<213> ORGANISM: artificial
<220> FEATURE:
<223> OTHER INFORMATION: artificial modified hinge region

<400> SEQUENCE: 45

```
Pro Ser Cys Cys Thr His Thr Cys Pro Pro Cys Pro
1               5                   10
```

<210> SEQ ID NO 46
<211> LENGTH: 12
<212> TYPE: PRT
<213> ORGANISM: artificial
<220> FEATURE:
<223> OTHER INFORMATION: artificial modified hinge region

<400> SEQUENCE: 46

```
Pro Ser Cys Asp Lys His Cys Cys Pro Pro Cys Pro
1               5                   10
```

<210> SEQ ID NO 47
<211> LENGTH: 11
<212> TYPE: PRT
<213> ORGANISM: artificial
<220> FEATURE:
<223> OTHER INFORMATION: artificial modified hinge region

<400> SEQUENCE: 47

```
Pro Lys Ser Thr His Thr Cys Pro Pro Cys Pro
1               5                   10
```

<210> SEQ ID NO 48
<211> LENGTH: 10
<212> TYPE: PRT
<213> ORGANISM: artificial
<220> FEATURE:
<223> OTHER INFORMATION: artificial modified hinge region

<400> SEQUENCE: 48

```
Pro Lys Ser Cys Thr Cys Pro Pro Cys Pro
1               5                   10
```

<210> SEQ ID NO 49
<211> LENGTH: 14
<212> TYPE: PRT
<213> ORGANISM: artificial
<220> FEATURE:
<223> OTHER INFORMATION: artificial modified hinge region

<400> SEQUENCE: 49

```
Pro Lys Ser Cys Asp Lys Cys Val Glu Cys Pro Pro Cys Pro
```

<210> SEQ ID NO 50
<211> LENGTH: 42
<212> TYPE: DNA
<213> ORGANISM: artificial
<220> FEATURE:
<223> OTHER INFORMATION: artificial modified hinge region

<400> SEQUENCE: 50
tgcaagagct gcgacaagac ccacacctgt cccccctgcc ct                          42

<210> SEQ ID NO 51
<211> LENGTH: 42
<212> TYPE: DNA
<213> ORGANISM: artificial
<220> FEATURE:
<223> OTHER INFORMATION: artificial modified hinge region

<400> SEQUENCE: 51
ccctgcagct gcgacaagac ccacacctgt cccccctgcc ct                          42

<210> SEQ ID NO 52
<211> LENGTH: 42
<212> TYPE: DNA
<213> ORGANISM: artificial
<220> FEATURE:
<223> OTHER INFORMATION: artificial modified hinge region

<400> SEQUENCE: 52
cccaagtgct gcgacaagac ccacacctgt cccccctgcc ct                          42

<210> SEQ ID NO 53
<211> LENGTH: 42
<212> TYPE: DNA
<213> ORGANISM: artificial
<220> FEATURE:
<223> OTHER INFORMATION: artificial modified hinge region

<400> SEQUENCE: 53
cctaagagct gttgcaagac ccacacctgt cccccctgcc ct                          42

<210> SEQ ID NO 54
<211> LENGTH: 42
<212> TYPE: DNA
<213> ORGANISM: artificial
<220> FEATURE:
<223> OTHER INFORMATION: artificial modified hinge region

<400> SEQUENCE: 54
cccaagagct gcgactgcac ccacacctgt cccccctgcc ct                          42

<210> SEQ ID NO 55
<211> LENGTH: 42
<212> TYPE: DNA
<213> ORGANISM: artificial
<220> FEATURE:
<223> OTHER INFORMATION: artificial modified hinge region

<400> SEQUENCE: 55
cccaagagct gcgacaagtg ccacacctgt cccccctgcc ct                          42

<210> SEQ ID NO 56
<211> LENGTH: 42
<212> TYPE: DNA
<213> ORGANISM: artificial

```
<220> FEATURE:
<223> OTHER INFORMATION: artificial modified hinge region

<400> SEQUENCE: 56
cccaagagct gcgacaagac ctgtacctgt cccccctgcc ct                              42

<210> SEQ ID NO 57
<211> LENGTH: 42
<212> TYPE: DNA
<213> ORGANISM: artificial
<220> FEATURE:
<223> OTHER INFORMATION: artificial modified hinge region

<400> SEQUENCE: 57
cccaagagct gcgacaagac ccactgctgt cccccctgcc ct                              42

<210> SEQ ID NO 58
<211> LENGTH: 42
<212> TYPE: DNA
<213> ORGANISM: artificial
<220> FEATURE:
<223> OTHER INFORMATION: artificial modified hinge region

<400> SEQUENCE: 58
cccaagagct gcgacaagac ccacacctgt tgcccctgcc ct                              42

<210> SEQ ID NO 59
<211> LENGTH: 42
<212> TYPE: DNA
<213> ORGANISM: artificial
<220> FEATURE:
<223> OTHER INFORMATION: artificial modified hinge region

<400> SEQUENCE: 59
cccaagagct gcgacaagac ccacacctgt ccctgctgcc ct                              42

<210> SEQ ID NO 60
<211> LENGTH: 42
<212> TYPE: DNA
<213> ORGANISM: artificial
<220> FEATURE:
<223> OTHER INFORMATION: artificial modified hinge region

<400> SEQUENCE: 60
cccaagagct gcgacaagac ccacacctgt cccccttgct gc                              42

<210> SEQ ID NO 61
<211> LENGTH: 39
<212> TYPE: DNA
<213> ORGANISM: artificial
<220> FEATURE:
<223> OTHER INFORMATION: artificial modified hinge region

<400> SEQUENCE: 61
cccagctgcg acaagaccca cacctgtccc ccctgccct                                  39

<210> SEQ ID NO 62
<211> LENGTH: 39
<212> TYPE: DNA
<213> ORGANISM: artificial
<220> FEATURE:
<223> OTHER INFORMATION: artificial modified hinge region

<400> SEQUENCE: 62
cccaagagct gcgacaccca cacctgtccc ccctgccct                                  39
```

<210> SEQ ID NO 63
<211> LENGTH: 39
<212> TYPE: DNA
<213> ORGANISM: artificial
<220> FEATURE:
<223> OTHER INFORMATION: artificial modified hinge region

<400> SEQUENCE: 63
cccaagagct gcgacaagac ccactgcccc ccctgccct                              39

<210> SEQ ID NO 64
<211> LENGTH: 36
<212> TYPE: DNA
<213> ORGANISM: artificial
<220> FEATURE:
<223> OTHER INFORMATION: artificial modified hinge region

<400> SEQUENCE: 64
aagtgcgaca agacccacac ctgtcccccc tgccct                                 36

<210> SEQ ID NO 65
<211> LENGTH: 36
<212> TYPE: DNA
<213> ORGANISM: artificial
<220> FEATURE:
<223> OTHER INFORMATION: artificial modified hinge region

<400> SEQUENCE: 65
cccagctgca agacccacac ctgtcccccc tgccct                                 36

<210> SEQ ID NO 66
<211> LENGTH: 36
<212> TYPE: DNA
<213> ORGANISM: artificial
<220> FEATURE:
<223> OTHER INFORMATION: artificial modified hinge region

<400> SEQUENCE: 66
cccaagagct gcgacaccca ctgcccccc tgccct                                  36

<210> SEQ ID NO 67
<211> LENGTH: 36
<212> TYPE: DNA
<213> ORGANISM: artificial
<220> FEATURE:
<223> OTHER INFORMATION: artificial modified hinge region

<400> SEQUENCE: 67
cccaagagct gcacccacac ctgtccccccc tgccct                                36

<210> SEQ ID NO 68
<211> LENGTH: 36
<212> TYPE: DNA
<213> ORGANISM: artificial
<220> FEATURE:
<223> OTHER INFORMATION: artificial modified hinge region

<400> SEQUENCE: 68
cccaagagct gcgacaagac cacctgtccc tgccct                                 36

<210> SEQ ID NO 69
<211> LENGTH: 36
<212> TYPE: DNA
<213> ORGANISM: artificial
<220> FEATURE:
<223> OTHER INFORMATION: artificial modified hinge region

<400> SEQUENCE: 69
cccaagagct gcgacaagac ccactgcccc ccctgc                                     36

<210> SEQ ID NO 70
<211> LENGTH: 39
<212> TYPE: DNA
<213> ORGANISM: artificial
<220> FEATURE:
<223> OTHER INFORMATION: artificial modified hinge region

<400> SEQUENCE: 70
cccaagagct gcgactgcca cacctgtccc ccctgccct                                  39

<210> SEQ ID NO 71
<211> LENGTH: 39
<212> TYPE: DNA
<213> ORGANISM: artificial
<220> FEATURE:
<223> OTHER INFORMATION: artificial modified hinge region

<400> SEQUENCE: 71
cccaagagct gcgactgcac ccactgcccc ccctgccct                                  39

<210> SEQ ID NO 72
<211> LENGTH: 36
<212> TYPE: DNA
<213> ORGANISM: artificial
<220> FEATURE:
<223> OTHER INFORMATION: artificial modified hinge region

<400> SEQUENCE: 72
ccctgcagct gcaagcacac ctgtccccccc tgccct                                    36

<210> SEQ ID NO 73
<211> LENGTH: 36
<212> TYPE: DNA
<213> ORGANISM: artificial
<220> FEATURE:
<223> OTHER INFORMATION: artificial modified hinge region

<400> SEQUENCE: 73
cctagctgct gcacccacac ctgtcccccc tgccct                                     36

<210> SEQ ID NO 74
<211> LENGTH: 36
<212> TYPE: DNA
<213> ORGANISM: artificial
<220> FEATURE:
<223> OTHER INFORMATION: artificial modified hinge region

<400> SEQUENCE: 74
cccagctgcg acaagcactg ctgccccccc tgccct                                     36

<210> SEQ ID NO 75
<211> LENGTH: 33
<212> TYPE: DNA
<213> ORGANISM: artificial
<220> FEATURE:
<223> OTHER INFORMATION: artificial modified hinge region

<400> SEQUENCE: 75
cccaagagca cccacacctg tccccttgt cct                                         33

<210> SEQ ID NO 76

<210> SEQ ID NO 76
<211> LENGTH: 30
<212> TYPE: DNA
<213> ORGANISM: artificial
<220> FEATURE:
<223> OTHER INFORMATION: artificial modified hinge region

<400> SEQUENCE: 76
cccaagagct gcacctgtcc cccttgtcct                              30

<210> SEQ ID NO 77
<211> LENGTH: 42
<212> TYPE: DNA
<213> ORGANISM: artificial
<220> FEATURE:
<223> OTHER INFORMATION: artificial modified hinge region

<400> SEQUENCE: 77
cccaagagct gcgataagtg cgtggagtgc ccccttgtc ct                 42

<210> SEQ ID NO 78
<211> LENGTH: 445
<212> TYPE: PRT
<213> ORGANISM: Artificial
<220> FEATURE:
<223> OTHER INFORMATION: artificial modified hinge region

<400> SEQUENCE: 78

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Pro Lys Ser Cys Asp Cys His
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

```
Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 79
<211> LENGTH: 446
<212> TYPE: PRT
<213> ORGANISM: Artificial
<220> FEATURE:
<223> OTHER INFORMATION: artificial modified hinge region

<400> SEQUENCE: 79

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
                20                  25                  30

Thr Met His Trp Val Arg Gln Ser Leu Gly Glu Ser Leu Asp Trp Ile
            35                  40                  45

Gly Gly Ile Lys Pro Asn Asn Gly Leu Ala Asn Tyr Asn Gln Lys Phe
        50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Pro Lys Ser Cys Asp Cys His
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 80
<211> LENGTH: 1338
<212> TYPE: DNA
<213> ORGANISM: Artificial
<220> FEATURE:
<223> OTHER INFORMATION: artificial modified hinge region

<400> SEQUENCE: 80
gaggtccagc tgcagcagag cgggccagaa ctggttaaac ctggcgccag cgtgaagatt     60
agctgtaaga ccagcggtta catctttaca gcatatacca tgcactgggt gaggcagagt    120
ctgggggaat ctctggactg gatcggaggt attaagccca acaatggcct ggctaactat    180
aatcaaaaat tcaagggcaa agccacactg accgtcgata gtcctcttca cacagcttac    240
atggatctga aagcctgac atccgaggac agtgcagtgt actactgcgc ccggtctgag    300
atcactaccg agttcgacta ttggggacag ggcactgcac tgaccgtctc ctccgccagc    360
accaagggcc caagcgtgtt cccgctagcc ccctgcagca gaagcaccag cgagagcaca    420

```
gccgccctgg gctgcctggt caaggactac ttccccgagc ccgtgaccgt gtcttggaac      480
agcggagccc tgaccagcgg cgtgcacacc tttccagccg tgctgcagag cagcggcctg      540
tacagcctga gcagcgtggt gacagtgccc agcagcaact tcggcaccca gacctacacc      600
tgtaacgtgg accacaagcc cagcaacacc aaggtggaca gaccgtgga gcccaagagc       660 tgcgattgcc actgcccccc ttgtcctgct cctcctgtgg ccggaccag cgtgttcctg       720 ttccccccaa agcccaagga caccctgatg atcagccgga ccccgaagt gacctgcgtg       780 gtggtggacg tgtcccacga ggaccccgag gtgcagttca attggtacgt ggacggcgtg      840
gaggtgcaca acgccaagac caagcccgg gaggaacagt tcaacagcac cttccgggtg       900
gtgtccgtgc tgaccgtggt gcaccaggac tggctgaacg gcaaagagta caagtgcaag      960
gtctccaaca agggcctgcc tgcccccatc gagaaaacca tcagcaagac caagggccag     1020
cctcgggagc ctcaggtgta caccctgccc ccagccggga ggaaatgac caagaaccag      1080 gtgtccctga cctgtctggt gaaaggcttc taccccagcg atatcgccgt ggagtgggag     1140
agcaacggcc agcccgagaa caactacaag accaccccc ccatgctgga cagcgacggc      1200
agcttcttcc tgtactccaa actgaccgtg gataagagcc ggtggcagca gggcaacgtg     1260
ttcagctgca gcgtgatgca cgaggccctg cacaaccact acacccagaa gtccctgagc     1320
ctgagccccg gcaaatga                                                   1338
```

<210> SEQ ID NO 81
<211> LENGTH: 1341
<212> TYPE: DNA
<213> ORGANISM: Artificial
<220> FEATURE:
<223> OTHER INFORMATION: artificial modified hinge region

<400> SEQUENCE: 81

```
gaggtccagc tgcagcagag cgggccagaa ctggttaaac ctggcgccag cgtgaagatt       60
agctgtaaga ccagcggtta catctttaca gcatatacca tgcactgggt gaggcagagt      120 ctggggaat ctctggactg gatcggaggt attaagccca caatggcct ggctaactat        180 aatcaaaaat tcaagggcaa agccacactg accgtcgata gtcctcttc cacagcttac      240 atggatctga aagcctgac atccgaggac agtgcagtgt actactgcgc ccggtctgag      300
atcactaccg agttcgacta ttggggacag ggcactgcac tgaccgtctc ctccgccagc      360
accaagggcc caagcgtgtt cccgctagcc ccctgcagca gaagcaccag cgagagcaca      420
gccgccctgg gctgcctggt gaaggactac ttccccgagc ccgtgaccgt gtcttggaac      480
agcggagccc tgaccagcgg cgtgcacacc tttccagccg tgctgcagag cagcggcctg      540
tacagcctga gcagcgtggt gacagtgcct agcagcagcc tgggcaccaa gacctacacc      600
tgtaacgtgg accacaagcc cagcaacacc aaggtggaca gcgggtgga gcccaagagc       660 tgcgattgcc actgcccccc ttgccctgcc cctgagttcc tggcggacc cagcgtgttc       720 ctgttccccc caaagcccaa ggacaccctg atgatcagcc ggaccccga agtgacctgc       780 gtggtggtgg acgtgtccca ggaagatccc gaggtgcagt tcaactggta cgtggacggc      840
gtggaggtgc acaacgccaa gaccaagccc cgggaggaac agttcaacag cacctaccgg      900
gtggtgtccg tgctgaccgt gctgcaccag gactggctga acggcaaaga gtacaagtgc      960
aaggtgtcca acaagggcct gcccagcagc atcgagaaaa ccatcagcaa ggccaagggc     1020
cagcctagag aaccccaggt gtacaccctg ccccccagcc aggaagagat gaccaagaac     1080
```

-continued

```
caggtgtccc tgacctgtct ggtgaaaggc ttctacccca gcgatatcgc cgtggagtgg   1140
gagagcaacg gccagcccga gaacaactac aagaccaccc cccctgtgct ggacagcgac   1200
ggcagcttct tcctgtactc ccggctgacc gtggacaaga gccggtggca ggaaggcaac   1260
gtgttcagct gcagcgtgat gcacgaggcc ctgcacaacc actacaccca gaagtccctg   1320
agcctgagcc tgggcaaatg a                                              1341
```